United States Patent
Nguyen et al.

(10) Patent No.: US 12,116,563 B2
(45) Date of Patent: *Oct. 15, 2024

(54) GAS-FED FERMENTATION REACTORS, SYSTEMS AND PROCESSES

(71) Applicant: Calysta, Inc., San Mateo, CA (US)

(72) Inventors: Luan Thanh Nguyen, San Ramon, CA (US); Arild Johannessen, Sandnes (NO); Graham Ian Aylen, Knowbury (GB); Joshua A. Silverman, Los Altos Hills, CA (US)

(73) Assignee: Calysta, Inc., San Mateo, CA (US)

( * ) Notice: Subject to any disclaimer, the term of this patent is extended or adjusted under 35 U.S.C. 154(b) by 229 days.

This patent is subject to a terminal disclaimer.

(21) Appl. No.: 17/732,263

(22) Filed: Apr. 28, 2022

(65) Prior Publication Data

US 2022/0259548 A1 Aug. 18, 2022

Related U.S. Application Data

(60) Division of application No. 16/774,991, filed on Jan. 28, 2020, now Pat. No. 11,332,706, which is a
(Continued)

(51) Int. Cl.
*C12M 1/00* (2006.01)
*C12M 1/34* (2006.01)
(Continued)

(52) U.S. Cl.
CPC ............ *C12M 45/04* (2013.01); *C12M 21/00* (2013.01); *C12M 29/00* (2013.01); *C12M 29/18* (2013.01);
(Continued)

(58) Field of Classification Search
CPC ...... C12M 21/00; C12M 21/02; C12M 29/00; C12M 29/18; C12M 29/20; C12M 35/08; C12M 41/40; C12M 45/04; C12N 1/30
(Continued)

(56) References Cited

U.S. PATENT DOCUMENTS 4,130,365 A 12/1978 Sittig
4,419,109 A 12/1983 Matula
(Continued)

FOREIGN PATENT DOCUMENTS

CN 2279200 Y 4/1998
CN 101396628 A 4/2009
(Continued)

OTHER PUBLICATIONS

Al Taweel et al., "Effect of Mixing on Microorganism Growth in Loop Bioreactors," *International Journal of Chemical Engineering 2012*: 2012, 12 pages.
(Continued)

*Primary Examiner* — Claire A Norris
(74) *Attorney, Agent, or Firm* — Seed IP Law Group LLP

(57) ABSTRACT

Reactors, systems and processes for the production of biomass by culturing microorganisms in aqueous liquid culture medium circulating inner loop reactor which utilize nonvertical pressure reduction zones are described. Recovery and processing of the culture microorganisms to obtain products, such as proteins or hydrocarbons is described.

18 Claims, 7 Drawing Sheets

Related U.S. Application Data continuation of application No. 15/625,858, filed on Jun. 16, 2017, now Pat. No. 10,570,364.

(60) Provisional application No. 62/351,668, filed on Jun. 17, 2016.

(51) Int. Cl.
  *C12M 1/42* (2006.01)
  *C12N 1/30* (2006.01)

(52) U.S. Cl.
  CPC ............ *C12M 29/20* (2013.01); *C12M 35/08* (2013.01); *C12M 41/40* (2013.01); *C12N 1/30* (2013.01); *C12M 21/02* (2013.01)

(58) Field of Classification Search
  USPC ........................................................ 210/603
  See application file for complete search history.

(56) References Cited

U.S. PATENT DOCUMENTS

| | | | |
|---|---|---|---|
| 4,530,760 | A | 7/1985 | Shimura |
| 4,530,762 | A | 7/1985 | Love |
| 4,704,363 | A | 11/1987 | Ziegler |
| 4,782,024 | A | 11/1988 | Scott et al. |
| 4,906,574 | A | 3/1990 | Erdei et al. |
| 5,073,496 | A | 12/1991 | Oosterhuis et al. |
| 6,279,882 | B1 | 8/2001 | Littman et al. |
| 6,492,135 | B1 | 12/2002 | Larsen |
| 6,689,601 | B2 | 2/2004 | Koffas et al. |
| 7,575,163 | B2 | 8/2009 | Malik |
| 7,579,163 | B2 | 8/2009 | Eriksen et al. |
| 8,354,063 | B2 * | 1/2013 | Hottovy ................. B01J 8/0015 422/135 |
| 8,648,209 | B1 | 2/2014 | Lastella |
| 9,114,357 | B2 | 8/2015 | Block et al. |
| 10,077,124 | B2 | 9/2018 | Suenaga et al. |
| 10,184,103 | B2 | 1/2019 | Larsen |
| 10,538,730 | B2 | 1/2020 | Nguyen et al. |
| 10,570,364 | B2 | 2/2020 | Nguyen et al. |
| 10,689,610 | B2 | 6/2020 | Nguyen et al. |
| 11,034,930 | B2 | 6/2021 | Nguyen et al. |
| 11,332,706 | B2 | 5/2022 | Nguyen et al. |
| 2004/0241790 | A1 * | 12/2004 | Eriksen .................... A23J 1/005 435/252.1 |
| 2005/0239182 | A1 | 10/2005 | Berzin |
| 2005/0272891 | A1 * | 12/2005 | Fouarge ............... G05D 11/132 526/170 |
| 2007/0003602 | A1 | 1/2007 | Johannessen et al. |
| 2008/0248552 | A1 | 10/2008 | Castillo Fernandez |
| 2009/0263877 | A1 | 10/2009 | Eriksen et al. |
| 2010/0068779 | A1 | 3/2010 | Wells et al. |
| 2011/0027875 | A1 | 2/2011 | Cathcart |
| 2011/0174159 | A1 | 7/2011 | Swantner et al. |
| 2011/0244543 | A1 | 10/2011 | Larsen |
| 2012/0021498 | A1 | 1/2012 | Muller-Feuga |
| 2012/0053304 | A1 | 3/2012 | Fouarge et al. |
| 2014/0017769 | A1 | 1/2014 | Schuessler et al. |
| 2015/0259639 | A1 | 9/2015 | Silverman et al. |
| 2016/0272524 | A1 | 9/2016 | Holm |
| 2017/0362562 | A1 | 12/2017 | Nguyen et al. |
| 2019/0048308 | A1 | 2/2019 | Nguyen et al. |
| 2019/0264164 | A1 | 8/2019 | Nguyen et al. |
| 2019/0352592 | A1 | 11/2019 | Nguyen et al. |
| 2020/0205440 | A1 | 7/2020 | Silverman et al. |
| 2020/0263123 | A1 | 8/2020 | Nguyen et al. |
| 2021/0261906 | A1 | 8/2021 | Nguyen et al. |
| 2022/0049207 | A1 | 2/2022 | Nguyen et al. |

FOREIGN PATENT DOCUMENTS

| | | |
|---|---|---|
| CN | 101683576 A | 3/2010 |
| CN | 102198984 A | 9/2011 |
| CN | 103657158 A | 3/2014 |
| CN | 106861243 A | 6/2017 |
| EP | 0185407 B1 | 1/1990 |
| EP | 0418187 A1 | 3/1991 |
| EP | 1183326 B1 | 3/2007 |
| EP | 2789396 A1 | 10/2014 |
| RU | 2 580 646 C1 | 4/2016 |
| WO | WO 0070014 A1 | 11/2000 |
| WO | WO 0160974 A2 | 8/2001 |
| WO | WO 0218617 A2 | 3/2002 |
| WO | WO 0220728 A2 | 3/2002 |
| WO | WO 0220733 A2 | 3/2002 |
| WO | WO 03016460 A1 | 2/2003 |
| WO | WO 2010056461 A2 | 5/2010 |
| WO | WO 2010069313 A2 | 6/2010 |
| WO | WO 2011018473 A2 | 2/2011 |
| WO | WO 2014058761 A1 | 4/2014 |
| WO | WO 2014060778 A1 | 4/2014 |
| WO | WO 2015179176 A1 | 11/2015 |
| WO | WO 2017218978 A1 | 12/2017 |

OTHER PUBLICATIONS

Petersen et al., "Mixing and Mass Transfer in a Pilot Scale U-Loop Bioreactor," *Biotechnology and Bioengineering* 114(2):344-354, Feb. 2017.

Spath et al., "Preliminary Screening—Technical and Economic Assessment of Synthesis Gas to Fuels and Chemicals with Emphasis on the Potential for Biomass-Derived Syngas," NREL/TP-510-34929, National Renewable Energy Laboratory, Golden, Co., Dec. 2003, 160 pages.

Sulter et al., "Proliferation and metabolic significance of peroxisomes in *Candida boidinii* during growth on D-alanine or oleic acid as the sole carbon source," *Arch Microbiol* 153:485-489, 1990.

Van Dien et al., "Reconstruction of C3 and C4 metabolism in Methylobacterium extorquens AMI using transposon mutagenesis," *Microbiology* 149:601-609, 2003.

* cited by examiner

ND PROCESSES

BACKGROUND

Technical Field

This invention is related to reactors, systems and processes useful in fermentation and, in particular, fermentation systems using a gaseous substrate.

Description of the Related Art

With the ever increasing depletion of fossil fuel deposits, the increasing production of greenhouse gases and recent concerns about climate change, substituting biofuels (e.g., ethanol, biodiesel) for fossil fuels has become an industrial focus. However, biofuels generated to date have their own difficulties and concerns. First generation biofuels are derived from plants (e.g., starch; cane sugar; and corn, rapeseed, soybean, palm, and other vegetable oils), but these fuel crops compete with crops grown for human and animal consumption. The amount of globally available farm land is insufficient to satisfy the increasing needs for both food and fuel. To reduce the demand placed upon food producers for biofuel compatible grains, second generation biofuels using alternative biological material such as cellulose or algae are under development. However, technical difficulties in production, along with the high cost of production, have not made second generation biofuels any more cost-effective or accessible.

Third or next generation biofuels are made using alternative, non-food based, carbon feedstocks. As part of this effort, the use of alternative, non-biological based, feedstocks in the production of higher hydrocarbon compounds including fuels, lubricants, and plastics is gaining ever-increasing momentum. Such feedstocks may include one or more carbon-containing compounds or mixtures of carbon-containing and non-carbon-containing compounds that include, among others, methane and syngas. Methane, for example, is a relatively abundant, naturally occurring and found in many locations throughout the world. Methane is also produced during many biological decay processes, and thus may be captured from waste treatment and landfill facilities. For its relative abundance, methane is a potent greenhouse gas, having 23× the relative greenhouse gas contribution of $CO_2$. Historically, methane has been viewed as a somewhat valuable byproduct that is difficult to convert to higher value products or to transport to the marketplace from remote or stranded locations such as remote gas fields or off-shore production platforms. Methane from such sources, as well as the methane produced by biological decomposition processes occurring at sewage treatment facilities and landfills, is primarily either vented or flared. The ability to economically and efficiently convert methane and similar carbon-containing gases to one or more higher value $C_2$ or higher hydrocarbons would permit producers to take advantage of a relatively abundant, non-biologically produced, feedstock while, at the same time, providing a significant environmental benefit.

The rise in domestic production of methane capability makes methane more readily available domestically. Domestic natural gas is primarily produced by hydraulic fracturing ("fracking"), but methane can also be obtained from other sources, such as landfills and sewage. But methane's volatility makes the transport and/or direct usage of methane as a fuel problematic.

For these reasons, a strong incentive exists to convert the methane to one or more liquid products, for example motor fuels, to permit easier transport to the point of use or sale. Two main approaches are currently being pursued: liquefaction leading to liquefied natural gas (LNG) and chemical conversion to convert gas-to-liquid (GTL) (Patel, 2005, 7th World Congress of Chemical Engineering, Glasgow, Scotland, UK). The Fischer Tropsch (F-T) process is currently the most prevalent approach for converting large quantities of methane to higher-order hydrocarbons (Patel, 2005). Note that the F-T process takes syngas as an input; syngas is produced from natural gas by steam reforming (syngas can also be sourced from coal gasification, by high temperature reaction with water and oxygen). The F-T process yields petroleum products consistent with today's fuel supply, but suffers from a number of drawbacks, including low yields, poor selectivity (making downstream utilization complex), and requires significant capital expenditure and scale to achieve economical production (Spath and Dayton, December 2003 NREL1TP-510-34929). The massive scale required for a F-T plant (generally in excess of two billion dollars in capital cost [Patel, 2005]) also represents a significant limitation due to the large amount of methane feedstock required to offset the enormous capital cost of the F-T process. As methane transportation is prohibitively expensive in most cases, such a plant must be co-located with a steady, reliable, and cost efficient source of methane, usually in the form of a significant methane reservoir or a methane pipeline. An additional cost and scaling factor is the economics of gas-scrubbing technologies (Spath and Dayton, 2003), since F-T catalysts are quite sensitive to common contaminants found in natural gas that pass unaffected through the syngas conversion process.

The requirements for ready access to large volumes of a relatively clean methane-containing gas, combined with a massive capital investment, currently limit natural gas based F-T plants to successful and economically viable operation in only a few locations worldwide (Spath and Dayton, 2003). The high minimum processing requirement for a gas-to-liquids process or liquefied natural gas plant, combined with the high cost of transport, result in smaller methane sources remaining as "stranded" gas deposits. Such stranded gas can include, but is not limited to, natural gas produced at off-shore oil wells, or methane off-gas from landfills. Due to the current absence of efficient small-scale conversion technologies, such stranded gas sources are typically vented to atmosphere or flared, as methane accumulation presents a significant safety risk. Gas-to-liquids facilities using the Fischer-Tropsch process have been in operation semi-continuously since 1938. Several companies are currently investigating introduction of new plants given the current availability and price of methane discussed above. However, despite significant research and development over the last 70+ years, the limitations of Fischer-Tropsch technology prevent broad adoption of commercial gas-to-liquids processes.

Advances in the efficiency in animal feed utilization have been achieved over the past several decades through the use of feed additives. These added substances augment the nutrient content, energy content, and/or disease fighting properties of animal feed compositions. A growing challenge for commercial animal producers is the rising cost of grain. The rising costs are due in part to competing demands for grains for biofuel and human food use. With the rising cost of grain and protein complements, coupled with limited land available for feed production, alternative low-cost animal feed products with beneficial nutritive and disease fighting properties are desirable.

A number of different protein-containing materials have been proposed as substitutes for more traditional sources of protein, such as fish meal, soya products and blood plasma, in human foods and as animal feed. These protein-containing materials include single cell microorganisms such as fungi, yeasts and bacteria which contain high proportions of proteins. These microorganisms may be grown on hydrocarbon or other substrates.

In view of the above, biological fermentation using $C_1$ substrates as a carbon source presents an attractive solution to both the current competition between food sources and fermentation for producing chemicals/fuels, the need for alternative low-cost animal feed products, as well as the lack of good options for utilization of natural gas. However, fermentation of gaseous substrates such as methane, CO, or $CO_2$ presents significant challenges due to the requirement that the carbon substrate must be transferred from the gas phase to an aqueous phase to allow for uptake and metabolism by the $C_1$ metabolizing non-photosynthetic microorganisms in culture. Simultaneously, other gasses such as $O_2$ or $H_2$ may also be required to be transferred from the gas phase to allow cellular metabolism to progress (aerobic or anaerobic metabolism, respectively). Waste products (such as $CO_2$ in the case of aerobic metabolism) must be isolated from the microorganisms to allow for efficient microbial growth. Further, the heat generation from metabolism of $C_1$ substrates is significant and the system requires cooling to maintain optimal conditions for microbial growth.

Convective mass transfer from the liquid phase to the vapor phase can be described with a mass transfer coefficient. The flux is equal to the product of the mass transfer coefficient, the surface area, and the concentration difference (Flux=k A $\Delta$C).

The mass transfer coefficient is influenced by a variety of factors including the size of the molecule to be transferred, its solubility in the aqueous phase, and the size of the boundary layer between the phases (typically controlled in fermentation systems by mixing speed and turbulence). The surface area between the gas and liquid phases in most fermentation systems is primarily limited by the bubble size of the input gas. Bubble size can be controlled by introducing the gas through small pores, as well as increasing shear forces to break apart bubbles and prevent coalescence. The concentration difference can be the concentration difference across the gas phase boundary layer, the concentration difference across the liquid phase boundary layer, the concentration difference between the bulk vapor and the vapor which would be in equilibrium with the bulk liquid, or the concentration difference between the bulk liquid and the liquid which would be in equilibrium with the bulk vapor. In most fermentation systems, the concentration difference is controlled by the pressure of the gas phase.

Conventional fermentation systems (bioreactors) achieve gas mixing by one of two methods: stirring or airlift. Stirred fermentors achieve mixing by means of stirring blades generally placed centrally in a single large fermentor. The stirrer blades generate turbulence and shear in the liquid while gas bubbles are introduced at the bottom of the fermentor, thus impeding the progress of the bubbles as they travel up the fermentor and shearing the gas bubbles to reduce the tendency of the bubbles to coalesce within the fermentor. The advantage of this type of fermentor is the fast, relatively homogeneous mixing and gas bubble dispersion that is possible due to the high speed of the mixing blades. However, this type of fermentor can be difficult to scale-up, as the energy requirements to obtain the same rate of mixing and mass transport can be prohibitive as the volume increases. Further, the vigorous mixing implies a significant heating of the fermentation liquid, and the use of a single large fermentor limits the surface area available for heat exchange cooling.

Airlift fermentors avoid mechanical stirrers by incorporating a flow path for the liquid. Airlift fermentors have a downflow and an upflow section which are interconnected at both ends; these sections can either be separate units (referred to as a loop fermentor), or concentric (airlift fermentor). In airlift fermentors, gasses are supplied at the bottom of the upflow section through a bubble-generating apparatus. The bubbles mix with the liquid, reducing the density of the liquid and causing the gas-liquid mixture to rise through the upflow section. The rising mixture displaces liquid at the top of the reactor, which travels down the downflow section to replace the liquid at the bottom, establishing a circular flow in the fermentor. In order to obtain a long residence time for the gas bubbles in the liquid, airlift fermentors are generally tall and have a limited transverse cross-sectional area. This implies that the gas must be supplied at a relatively high pressure to overcome hydrostatic pressure formed by the column of liquid present in the fermentor. In addition, the bubble size increases significantly throughout the fermentor as the pressure decreases with height. The increasing bubble diameter proportionately reduces the rate of mass transfer between the gas bubbles and the liquid phase by reducing the ratio of gas bubble area (proportionate to the square of the gas bubble radius) to gas bubble volume (proportionate to the cube of the gas bubble radius) through which mass transfer may occur. Flow rates and shear forces in airlift fermentors are significantly lower than in stirred tank fermentors, which also tend to increase bubble coalescence and reduce the efficiency of cooling the fermentor. Finally, separation of the unused and waste gases from the mixture exiting the upflow portion of the fermentor prior to the return of the liquid to the downflow section can be challenging.

Loop reactors are described in U.S. Pat. No. 7,575,163 and have been proposed for fermenting microorganisms, e.g., for the generation of biomass or for the preparation of materials produced by microorganisms. FIG. 1 illustrates one loop reactor 1 including an effluent gas removal zone 2 which flows into a vertical downflow zone 3. Effluent gas removal zone 2 includes an outlet port 7 and an emergency vent 8. Vertical downflow zone 3 includes a nutrient gas inlet 15. A propeller 10 powered by motor 11 assists in circulation of a liquid culture medium through the loop reactor. Upstream of propeller 10 is an exit port 12 for removing material from the loop reactor. Downstream of propeller 10 are ammonia and mineral inlets 17 and 18. Liquid culture medium 9 passes through a plurality of static mixers 14 in a horizontal section 4 of the loop reactor. The horizontal section of the loop reactor also includes a plurality of nutrient gas inlets 13. Downstream of the last static mixer 14, the loop reactor includes a vertical upflow section 5. The top end of vertical upflow section 5 fluidly communicates with a horizontal outflow zone 6. Vertical upflow section 5 is provided with a nutrient gas inlet 16. Downstream of nutrient gas inlet 16 is a drive gas inlet 19 through which a driving gas is delivered to the liquid culture medium. The '163 patent describes the loop reactor illustrated in FIG. 1 has a vertical drop between the gas-liquid surface at the end of the outflow zone 6 and the centerline of the loop in the horizontal section that is at least 10 meters.

BRIEF SUMMARY

In one aspect, the present disclosure describes systems, processes and apparatuses for efficient mass transfer of gaseous substrates for microbial fermentation. Additionally, this disclosure describes systems, processes and apparatuses for fermenting gaseous carbon-containing feedstocks using a culture primarily comprising a $C_1$ metabolizing non-photosynthetic microorganism. In other aspects, this disclosure describes systems, processes and apparatuses for fermenting gaseous feedstocks which include gaseous substrates, using other than $C_1$ metabolizing non-photosynthetic microorganism(s). In yet another aspect, this disclosure describes scalable fermentor designs for allowing high flux gas-phase to liquid-phase mass transfer in addition to efficient heat exchange and waste gas removal. Systems and processes for fermentation that overcome disadvantages known in the art and provide the public with new processes and devices for the optimal production of a variety of products are described.

Such fermentation systems may employ one or more species of microorganism that are capable of metabolizing gaseous compounds; for example, $C_1$ compounds. Such microorganisms include prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas*, or *Pseudomonas*. In some instances, the $C_1$ metabolizing microorganisms may include methanotrophs, methylotrophs or combinations thereof. Preferred methanotrophs include *Methylomonas, Methylobacter, Methylococcus, Methylosinus, Methylocystis, Methylomicrobium, Methanomonas*, or combinations thereof. Exemplary methanotrophs include *Methylomonas* sp. 16a (ATCC PTA 2402), *Methylosinus trichosporium* (NRRL B-11, 196), *Methylosinus sporium* (NRRL B-11, 197), *Methylocystis parvus* (NRRL B-11, 198), *Methylomonas methanica* (NRRL B-5 11,199), *Methylomonas albus* (NRRL B-11,200), *Methylobacter capsulatus* (NRRL B-11, 201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylosinus trichosporium* OB3b, *Methylococcus capsulatus* Bath, *Methylomonas* sp. 16a, *Methylomicrobium alcaliphilum* 20Z, or high growth variants thereof. Preferred methylotrophs include *Methylobacterium extorquens, Methylobacterium radiotolerans, Methylobacterium populi, Methylobacterium chloromethanicum, Methylobacterium nodulans*, or combinations thereof.

Microorganisms capable of metabolizing $C_1$ compounds found in syngas include, but are not limited to *Clostridium, Moorella, Pyrococcus, Eubacterium, Desulfobacterium, Carboxydothermus, Acetogenium, Acetobacterium, Acetoanaerobium, Butyribacterium, Peptostreptococcus*, or combinations thereof. Exemplary methylotrophs include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or combinations thereof. In some instances, $C_1$ metabolizing microorganisms are eukaryotes such as yeast, including *Candida, Yarrowia, Hansenula, Pichia, Torulopsis*, or *Rhodotorula*.

In other instances, the $C_1$ metabolizing non-photosynthetic microorganism is an obligate $C_1$ metabolizing non-photosynthetic microorganism, such as an obligate methanotroph, an obligate methylotroph, or combinations thereof. In some instances, the $C_1$ metabolizing non-photosynthetic microorganism is a recombinant microorganism comprising a heterologous polynucleotide encoding a fatty acid producing enzyme, a formaldehyde assimilation enzyme, or combinations thereof.

In addition or as alternatives to the above, the present disclosure describes the following embodiments. A first embodiment directed to a system for stimulating production of biomass that includes a loop reactor which includes a gas/liquid separation vessel for separating a multi-phase mixture of a gas and a liquid culture medium into a gas phase and a liquid phase, the gas/liquid separation vessel including an outlet and an inlet; a loop section including an inlet in fluid communication with the outlet of the gas/liquid separation vessel, an outlet in fluid communication with the inlet of the gas/liquid separation vessel and a loop section centerline; a first non-vertical pressure reduction zone including a first pressure reduction device, the first non-vertical pressure reduction zone located between the inlet of the loop section and the outlet of the loop section, a vertical distance between the loop section centerline at the inlet of the gas/liquid separation vessel and loop section centerline at the inlet of the loop section is less than 8 meters.

A second embodiment disclosed herein is directed to the first embodiment wherein the pressure reduction device is a valve or expansion joint.

A third embodiment disclosed herein is directed to the system of the first and second embodiments, including a second pressure reduction zone downstream of the first non-vertical pressure reduction zone.

A fourth embodiment disclosed herein is directed to the first through third embodiments wherein the second pressure reduction zone is a second non-vertical pressure reduction zone.

A fifth embodiment disclosed herein is directed to the first through fourth embodiments wherein the vertical distance between the loop section centerline at the inlet of the gas/liquid separation vessel and the loop section centerline at the inlet of the loop section is less than 6 meters.

A sixth embodiment disclosed herein is directed to the first through fifth embodiment wherein the vertical distance between the loop section centerline at the inlet of the gas/liquid separation vessel and the loop section centerline at the inlet of the loop section is less than 5 meters.

A seventh embodiment disclosed herein is directed to the first through sixth embodiments wherein the loop reactor further includes a desorption gas inlet, the desorption gas inlet located in a non-vertical portion of the loop section of the loop reactor.

An eighth embodiment disclosed herein is directed to the first through seventh embodiments wherein the first vertical pressure reduction device is a device that reduces pressure without relying upon a change in hydrostatic pressure.

A ninth embodiment disclosed herein is directed to a process for stimulating production of biomass including flowing through a loop section of a loop reactor, a multi-phase mixture of a gas and a liquid culture medium, the loop section including a loop section centerline; introducing nutrients into the multi-phase mixture; introducing methane and oxygen into the multi-phase mixture; passing the multi-phase mixture of a gas and a liquid culture medium through a first non-vertical pressure reduction zone of the loop reactor, the first non-vertical pressure reduction zone of the loop reactor including a first pressure reduction device; separating the multi-phase mixture of a gas and liquid culture medium into a gas phase and a liquid phase downstream of the first pressure reduction device; flowing the gas phase and the liquid phase separated from the multi-phase mixture of a gas and a liquid culture medium into a gas/ liquid separation vessel at an inlet to the gas/liquid separation vessel, the inlet to the gas/liquid separation vessel including a centerline; and removing the liquid phase from an outlet of the gas/liquid separation vessel and delivering the removed liquid phase to an inlet of the loop section, a vertical distance between the loop section centerline at the inlet of the loop section and the centerline of the inlet to the gas/liquid separation vessel being less than 8 meters.

A tenth embodiment described herein is directed to the ninth embodiment wherein passing the multi-phase mixture of a gas and a liquid culture medium to a first non-vertical pressure reduction zone includes passing the multi-phase mixture of a gas and a liquid culture medium through a valve, expansion joint, static mixer or piping elbow.

An eleventh embodiment described herein is directed to the ninth and tenth embodiments further including passing the multi-phase mixture of a gas and a liquid culture medium through a second pressure reduction zone downstream of the first non-vertical pressure reduction zone.

A twelfth embodiment described herein is directed to the ninth through eleventh embodiments wherein the vertical distance between the loop section centerline at the inlet of the loop section and the centerline of the inlet to the gas/liquid separation vessel is less than 6 meters.

A thirteenth embodiment described herein is directed to the ninth through twelfth embodiments wherein the vertical distance between the loop section centerline at the inlet of the loop section and the centerline of the inlet to the gas/liquid separation vessel is less than 5 meters.

A fourteenth embodiment described herein is directed to the ninth through thirteenth embodiments, further comprising introducing a desorption gas into a non-vertical portion of the loop section of the loop reactor.

A fifteenth embodiment described herein is directed to the ninth through fourteenth embodiments, further comprising passing the multi-phase mixture of a gas and a liquid culture medium through a first non-vertical pressure reduction zone, and includes passing the multi-phase mixture of a gas and a liquid culture medium through a device that reduces pressure without relying upon a change in hydrostatic pressure.

A sixteenth embodiment described herein is directed to a process for stimulating the production of biomass in a loop reactor including passing a multi-phase mixture of a gas and a liquid culture medium through a first non-vertical pressure reduction zone of the loop reactor, the first non-vertical pressure reduction zone of the loop reactor including a first pressure reduction device; separating the multi-phase mixture of a gas and a liquid culture medium into a gas phase and a liquid phase downstream of the first pressure reduction device; passing the gas phase and the liquid phase separated from the multi-phase mixture of a gas and a liquid culture medium into a gas/liquid separation vessel at an inlet to the gas/liquid separation vessel, the inlet to the gas/liquid separation vessel including a centerline; and removing a liquid phase from an outlet of the gas/liquid separation vessel and delivering the removed liquid phase to an inlet of a loop section of the loop reactor, a vertical distance between the loop section centerline at the inlet of the loop section and the centerline of the inlet to the gas/liquid separation vessel being less than 8 meters.

A seventeenth embodiment described herein is directed to the sixteenth embodiment wherein the vertical distance between the loop section centerline at the inlet of the loop section and the centerline of the inlet to the gas/liquid separation vessel is less than 6 meters.

An eighteenth embodiment described herein is directed to the sixteenth through seventeenth embodiments wherein the vertical distance between the loop section centerline at the inlet of the loop section and the centerline of the inlet to the gas/liquid separation vessel is less than 5 meters.

A nineteenth embodiment described herein is directed to the sixteenth through eighteenth embodiments wherein the first pressure reduction device is a device that reduces pressure without relying upon a change in hydrostatic pressure.

BRIEF DESCRIPTION OF THE SEVERAL VIEWS OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

DETAILED DESCRIPTION

Figure 1:
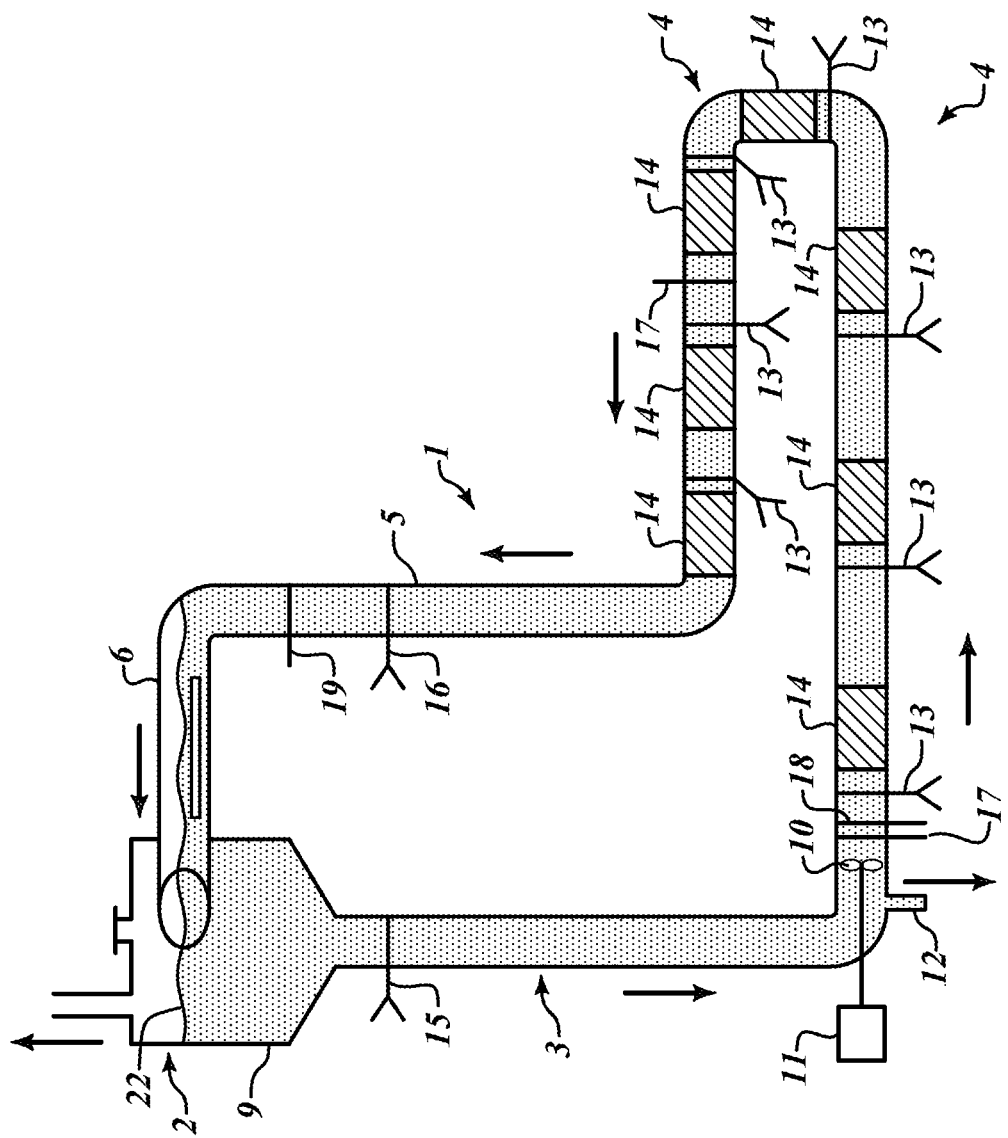
FIG. 1 shows a schematic view of a prior art loop reactor including a vertical upflow section upstream from an outflow zone where degassing occurs.

In the following description, certain specific details are set forth in order to provide a thorough understanding of various embodiments. However, one skilled in the art will understand that the invention may be practiced without these details. In other instances, structures, standard vessel design details, detailed design parameters of available components such as liquid or gas distributors, pumps, turbines, and similar, details concerning the design and construction of American Society of Mechanical Engineers (ASME) pressure vessels, control system theory, specific steps in one or more fermentation processes, and the like have not been shown or described in detail to avoid unnecessarily obscuring descriptions of the described embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Fermentors are generally defined as any vessel in which a fermentation process is carried out. Given the vast number of fermentation processes and the wide variety of fermentable substrates, fermentors can range from simple continuous stirred tank reactors found in the alcoholic beverage industry to highly complex, specialized vessels having gas distribution and internal structures tailored to a particular substrate and/or a particular biological species. Fermentors useful in converting carbon-containing gases such as methane and syngas (a mixture of CO and $H_2$) to longer chain gaseous and liquid hydrocarbons generally disperse a gas substrate containing the $C_1$ carbon compound within a liquid media containing one or more nutrients to provide a multi-phase mixture. This multi-phase mixture is fed to one or more microbiological colonies that convert a portion of the $C_1$ carbon compound(s) in the gas substrate to more preferred, longer chain, $C_2$ or higher compounds. The substrate composition, nutrients, and microbiological organisms comprising the colony (i.e., the biomass within the fermentor) can be variously adjusted or tailored to provide a desired final matrix of $C_2$ or higher compounds which may be present as a liquid, gas, or intracellular material.

Fermentors useful in utilizing carbon-containing gases such as methane and syngas (a mixture of CO and $H_2$) as a substrate for culturing single cell microorganisms such as fungi, yeasts and bacteria which contain high proportions of proteins generally disperse a gas substrate containing a $C_1$ carbon compound within a liquid media containing one or more nutrients to provide a multi-phase mixture. This multi-phase mixture is contacted with one or more microbiological colonies that convert a portion of the $C_1$ carbon compound(s) in the gas substrate to proteins. The substrate composition, nutrients, and microbiological organisms comprising the colony (i.e., the biomass within the fermentor) can be variously adjusted or tailored to provide a desired final matrix of protein-containing biomass.

From a mass transfer perspective, gas substrate fermentors present a unique challenge in that the substrate is trapped within a gas bubble and in order for microbiological uptake of the substrate to occur, the gas substrate must first pass from the gas bubble to the microbiological organisms either directly or indirectly via dissolution in the liquid media. Such fermentation processes are thus frequently limited by the ability of the system to facilitate and/or sustain a desirably high level of mass transfer of the substrate from the gas bubbles to the microbiological organisms within the fermentor. At the least, the rate of mass transfer from the gas bubble to either the surrounding liquid media or to a microbiological organisms is a function of the gas pressure within the gas bubble, the volume to surface area ratio of the gas bubble, and the contact time of the gas bubble with the surrounding liquid or microbiological organisms. Increasing the pressure within the gas bubble or increasing the contact time of the gas bubble with the surrounding liquid or microbiological organisms results in a higher effective mass transfer rate between the substrate and the microbiological organisms. Decreasing the volume to surface area ratio of the gas bubble (i.e., reducing the diameter of the gas bubbles) results in a higher effective mass transfer rate between the gas bubble and the surrounding liquid. Preferred fermentors from a mass transfer standpoint would therefore generate a large number of relatively small diameter gas bubbles at a relatively high pressure that are held in close or intimate contact with the surrounding liquid or microbiological organisms for an extended period of time.

Disclosed herein are a number of fermentation systems, methods, and apparatuses that are capable of providing relatively small diameter, relatively high pressure gas bubbles. Disclosed herein are a number of fermentation systems, methods, and apparatuses capable of providing an extended contact time with the surrounding liquid and/or biological organism(s). Such fermentation systems, methods, and apparatuses can advantageously provide a highly efficient gas substrate fermentation system that may be particularly useful in converting $C_1$ compounds to more preferred gaseous, liquid, and intra-cellular $C_2$ and higher compounds or stimulating the growth of microorganisms containing high proportions of protein.

As used herein, the terms "$C_1$ substrate" or "$C_1$ compound" refer to any carbon-containing molecule or composition that lacks a carbon-carbon bond. Sample $C_1$ molecules or compositions include methane, methanol, formaldehyde, formic acid or a salt thereof, carbon monoxide, carbon dioxide, syngas, methylamines (e.g., monomethylamine, dimethylamine, trimethylamine), methylthiols, or methylhalogens.

As used herein, the term "microorganism" refers to any microorganism having the ability to use a gaseous substrate as a source of energy or as its sole source of energy and biomass, and may or may not use other carbon substrates (such as sugars and complex carbohydrates) for energy and biomass. Examples of microorganisms as used herein include the heterotrophic bacteria *Ralstonia* sp. (formerly *Alcaligenes acidovorans*) DB3 (strain NCIMB 13287), *Brevibacillus agri* (formerly *Bacillus firmus*) DB5 (strain NCIMB 13289) and Aneurinibacillus sp. (formerly *Bacillus brevis*) DB4 (strain NCIMB 13288) which each have optimum growth at a temperature of about 45° C. *Ralstonia* sp. DB3 is a gram-negative, aerobic, motile rod belonging to the family Pseudomonadaceae which can use ethanol, acetate, propionate and butyrate for growth. Aneurinibacillus sp. DB4 is a gram-negative, endospore-forming, aerobic rod belonging to the genus *Bacillus* which can utilize acetate, D-fructose, D-mannose, ribose and D-tagatose. *Brevibacillus agri* DB5 is a gram-negative, endospore-forming, motile, aerobic rod of the genus *Bacillus* which can utilize acetate, N-acetyl-glucosamine, citrate, gluconate, D-glucose, glycerol and mannitol. Suitable yeasts for use in the processes of the invention may be selected from the group consisting of *Saccharomyces* and *Candida*.

If desired, the processes described herein may be performed using bacteria (or yeasts) genetically modified so as to generate a desired chemical compound which can then be extracted from the intercellular fluid or the biomass harvested from the reactor. The scientific and patent literature contains numerous examples of such genetically modified microorganisms including, inter alia, methanotrophic bacteria.

In at least some instances in accordance with embodiments described herein, the microbiological organisms used to ferment gaseous carbon-containing feedstocks employ a culture primarily comprising a $C_1$ metabolizing non-photosynthetic microorganism. Such fermentation systems may use one or more species of $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas*, or *Pseudomonas*. In some instances, the $C_1$ metabolizing bacteria may include a methanotroph or a methylotroph. Preferred methanotrophs include *Methylomonas, Methylobacter, Methylococcus, Methylosinus, Methylocystis, Methylomicrobium, Methanomonas*, or a combination thereof. Exemplary methanotrophs include *Methylomonas* sp. 16a (ATCC PTA 2402), *Methylosinus trichosporium* (NRRL B-11,196), *Methylosinus sporium* (NRRL B-11, 197), *Methylocystis parvus* (NRRL B-11, 198), *Methylomonas methanica* (NRRL B-5 11,199), *Methylomonas albus* (NRRL B-11,200), *Methylobacter capsulatus* (NRRL B-11,201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylosinus trichosporium* OB3b, *Methylococcus capsulatus* Bath, *Methylomonas* sp. 16a, *Methylomicrobium alcaliphilum* 20Z, or a high growth variants thereof. Preferred methylotrophs include *Methylobacterium extorquens, Methylobacterium radiotolerans, Methylobacterium populi, Methylobacterium chloromethanicum, Methylobacterium nodulans*, or a combination thereof.

Microorganisms capable of metabolizing $C_1$ compounds found in syngas include, but are not limited to *Clostridium, Moorella, Pyrococcus, Eubacterium, Desulfobacterium, Carboxydothermus, Acetogenium, Acetobacterium, Acetoanaerobium, Butyribacterium, Peptostreptococcus*, or combinations thereof may also be used. Exemplary methylotrophs include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or a combination thereof. In some instances, $C_1$ metabolizing microorganisms are eukaryotes such as yeast, including *Candida, Yarrowia, Hansenula, Pichia, Torulopsis*, or *Rhodotorula*.

In other instances, the $C_1$ metabolizing non-photosynthetic microorganism is an obligate $C_1$ metabolizing non-photosynthetic microorganism, such as an obligate methanotroph or methylotroph. In some instances, the $C_1$ metabolizing non-photosynthetic microorganism is a recombinant microorganism comprising a heterologous polynucleotide encoding a fatty acid producing enzyme, a formaldehyde assimilation enzyme, or a combination thereof.

As used herein, the terms "$C_1$ metabolizing microorganism" or "$C_1$ metabolizing non-photosynthetic microorganism" refer to any microorganism having the ability to use a single carbon ($C_1$) substrate as a source of energy or as its sole source of energy and biomass, and may or may not use other carbon substrates (such as sugars and complex carbohydrates) for energy and biomass. For example, a $C_1$ metabolizing microorganism may oxidize a $C_1$ substrate, such as methane or methanol. $C_1$ metabolizing microorganisms include bacteria (such as Methanotrophs and Methylotrophs) and yeast. In at least some instances, a $C_1$ metabolizing microorganism does not include a photosynthetic microorganism, such as algae. In certain embodiments, the $C_1$ metabolizing microorganism will be an "obligate $C_1$ metabolizing microorganism," meaning its sole source of energy comprises $C_1$ substrates and nothing else.

As used herein, the term "methylotrophic bacteria" refers to any bacteria capable of oxidizing organic compounds that do not contain carbon-carbon bonds. In certain embodiments, a methylotrophic bacterium may be a methanotroph. For example, "methanotrophic bacteria" refers to any methylotrophic bacteria that has the ability to oxidize methane as its primary source of carbon and energy. Exemplary methanotrophic bacteria include *Methylomonas, Methylobacter, Methylococcus, Methylosinus, Methylocystis, Methylomicrobium*, or *Methanomonas*. In certain other embodiments, the methylotrophic bacterium is an "obligate methylotrophic bacterium," which refers to bacteria that are limited to the use of $C_1$ substrates for the generation of energy.

In one specific embodiment of the invention, the process is performed using methanotrophic bacteria of the type described in WO 02/18617 to produce carotenoids, e.g., antheraxanthin, adonixanthin, astaxanthin, canthaxanthin, zeaxanthin and the other carotenoids mentioned on pages 39 and 40 of WO 02/18617. To this end, the methanotrophic bacterium *Methylomonas* 16a (ATCC PTA 2402) may particularly suitably be used. Carotenoids produced in this way may be separated out from the liquid culture medium as described in WO 02/18617, WO 02/20728 and WO 02/20733.

As used herein, the term "syngas" refers to a mixture including at least carbon monoxide (CO) and hydrogen ($H_2$). In at least some instances, syngas may also include $CO_2$, methane, and other gases in smaller quantities relative to CO and $H_2$. Syngas may be prepared using any available process, including but not limited to, a water gas shift or coal gasification process.

As used herein, the term "growth" is defined as any increase in cell mass. This may occur through cell division (replication) and the formation of new cells during "balanced growth," or during "unbalanced growth" when cellular mass increases due to the accumulation of one or more intracellular or intercellular polymers, such as certain lipids. In the latter case, growth may be manifest as an increase in cell size due to the accumulation of a biopolymer within the cell. During "balanced cell growth," all of the feedstocks (electron donors and electron acceptors) and all of the nutrients are present in the ratios required to make all of the macromolecular components of a cell. That is, no feedstock or nutrient limits the synthesis of proteins, complex carbohydrate polymers, fats, or nucleic acids. In contrast, during "unbalanced cell growth," a feedstock or nutrient needed to make one or more of a cell's macromolecules is not present in an amount or ratio required for balanced growth. Accordingly, this feedstock or nutrient becomes limiting and is referred to as a "limiting nutrient."

Some cells may still achieve net growth under unbalanced conditions, but the growth is unbalanced and polymers that can be synthesized in the absence of the limiting feedstock or nutrient will accumulate. These polymers include lipids or intracellular storage products, such as the polyhydroxyalkanoates (PHAs), including polyhydroxybutyrate (PHB), polyhydroxyvalerate (PHV), and polyhydroxyhexanoate (PHHx)-glycogen, or secreted materials, such as extracellular polysaccharide. Such oil compositions are useful in the production of bioplastics.

Sample balanced and unbalanced growth conditions may differ in the nitrogen content in the media. For example, nitrogen constitutes about 12% of dry cell weight, which means that 12 mg/L nitrogen must be supplied (along with a feedstock and other nutrients in the required stoichiometric ratios) to grow 100 mg/L dry cell weight. If other feedstock and nutrients are available in the quantities needed to produce 100 mg/L of dry cell weight, but less than 12 mg/L nitrogen is provided, then unbalanced cell growth may occur, with accumulation of polymers that do not contain nitrogen. If nitrogen is subsequently provided, the stored polymer may serve as feedstock for the cell, allowing balanced growth, with replication and production of new cells.

As used herein, the term "growth cycle" as applied to a cell or microorganism refers to the metabolic cycle through which a cell or microorganism moves in culture conditions. For example, the cycle may include various stages, such as a lag phase, an exponential phase, the end of exponential phase, and a stationary phase.

As used herein, the term "exponential growth," "exponential phase growth," "log phase" or "log phase growth" refer to the rate at which microorganisms are growing and dividing. For example, during log phase, microorganisms are growing at their maximal rate given their genetic potential, the nature of the medium, and the conditions under which they are grown. Microorganism rate of growth is constant during exponential phase and the microorganism divides and doubles in number at regular intervals. Cells that are "actively growing" are those that are growing in log phase. In contrast, "stationary phase" refers to the point in the growth cycle during which cell growth of a culture slows or even ceases.

As used herein, the term "high growth variant" refers to an organism, microorganism, bacterium, yeast, or cell capable of growth with a $C_1$ substrate, such as methane or methanol, as the sole carbon and energy source and which possesses an exponential phase growth rate that is faster than the parent, reference or wild-type organism, microorganism, bacterium, yeast, or cell—that is, the high growth variant has a faster doubling time and consequently a high rate of growth and yield of cell mass per gram of $C_1$ substrate metabolized as compared to a parent cell (see, e.g., U.S. Pat. No. 6,689,601).

As used herein, the term "biofuel" refers to a fuel at least partially derived from "biomass."

As used herein, the term "biomass" or "biological material" refers to organic material having a biological origin, which may include one or more of whole cells, lysed cells, extracellular material, or the like. For example, the material harvested from a cultured microorganism (e.g., bacterial or yeast culture) is considered the biomass, which can include cells, cell membranes, cell cytoplasm, inclusion bodies, products secreted or excreted into the culture medium, or any combination thereof. In certain embodiments, biomass comprises the $C_1$ metabolizing microorganisms of this disclosure together with the media of the culture in which the $C_1$ metabolizing microorganisms of this disclosure were grown. In other embodiments, biomass comprises $C_1$ metabolizing microorganisms (whole or lysed or both) of this disclosure recovered from a culture grown on a $C_1$ (e.g., natural gas, methane). In still other embodiments, biomass comprises the spent media supernatant or gases excreted or secreted from a culture of $C_1$ metabolizing microorganism culture on a $C_1$ substrate. Such a culture may be considered a renewable resource.

As used herein, the term "biorefinery" refers to a facility that integrates biomass conversion processes and equipment to produce fuels from biomass.

As used herein, "oil composition" refers to the lipid content of a biomass (e.g., bacterial culture), including fatty acids, fatty acid esters, triglycerides, phospholipids, poly hydroxyalkanoates, isoprenes, terpenes, or the like. In oil composition of a biomass may be extracted from the rest of the biomass materials, such as by hexane or chloroform extraction. In addition, an "oil composition" may be found in any one or more areas of a culture, including the cell membrane, cell cytoplasm, inclusion bodies, she treated or excreted into the culture medium, or any combination thereof. An oil composition is neither natural gas nor crude petroleum.

As used herein, the term "refinery" refers to an oil refinery, or aspects thereof, at which oil compositions (e.g., biomass, biofuel, or fossil fuels such as crude oil, coal or natural gas) may be processed. Sample processes carried out at such refineries include cracking, transesterification, reforming, distilling, hydroprocessing, isomerization, or any combination thereof.

As used herein, the terms "recombinant" or "non-natural" refer to an organism microorganism, cell, nucleic acid molecule, or vector that has at least one genetic alteration or has been modified by the introduction of a heterologous nucleic acid molecule, or refers to a cell that has been altered such that the expression of an endogenous nucleic acid molecule or gene can be controlled. Recombinant also refers to a cell that is derived from a cell having one or more such modifications. For example, recombinant cells may express genes or other nucleic acid molecules that are not found in identical form within the native cell (i.e., unmodified or wild type cell), or may provide an altered expression pattern of endogenous genes, such genes that may otherwise be over-expressed, under-expressed, minimally expressed, or not expressed at all. In another example, genetic modifications to nucleic acid molecules encoding enzymes or functional fragments thereof can provide biochemical reaction(s) or metabolic pathway capabilities to a recombinant microorganism or cell that is new or altered from its naturally occurring state.

As used herein, the term "heterologous" nucleic acid molecule, construct or sequence refers to a nucleic acid molecule or portion of a nucleic acid molecule sequence that is not native to a cell in which it is expressed or is a nucleic acid molecule with an altered expression as compared to the native expression levels in similar conditions. For example, a heterologous control sequence (e.g., promoter, enhancer) may be used to regulate expression of a gene or a nucleic acid molecule in a way that is different than the gene or a nucleic acid molecule is normally expressed in nature or culture. Generally, heterologous nucleic acid molecules are not endogenous to the cell or part of the genome in which they are present, and have been added to the cell by conjugation, transformation, transfection, electroporation, or the like.

As used herein, the term "vertical" refers to a direction that is aligned with the gravity vector at the location in question.

As used herein, the term "horizontal" refers to a direction that is perpendicular to the gravity vector at the location in question.

As used herein, the term "non-vertical" refers to a direction that is horizontal (i.e., perpendicular to vertical) or 20° or more from vertical, e.g., more than 20°, 25°, 30°, 35°, 40°, 45°, 50°, 55°, 60°, 65°, 70°, 75°, 80° or 85° from vertical.

The systems for fermentation of the instant disclosure may include separate units (e.g., processing units or systems that are disposed in close proximity or adjacent to each other, or not), integrated units, or the system itself may be interconnected and integrated. The systems of this disclosure may use at least one gas phase feedstock, including one or more $C_1$ compounds, oxygen, and/or hydrogen. In certain embodiments, the fermentation system uses a $C_1$ metabolizing microorganism (e.g., a methanotroph such as *Methylosinus trichosporium* OB3b, *Methylococcus capsulatus* Bath, *Methylomonas* sp. 16a, *Methylomicrobium alcaliphilum* 20Z, or high growth variants or combinations thereof) as the primary microorganism in the fermentation culture.

A variety of culture methodologies may be used for the microorganism, bacteria and yeast described herein. For example, $C_1$ metabolizing microorganisms, such as methanotroph or methylotroph bacteria, may be grown by batch culture and continuous culture methodologies. Generally cells in log phase are often responsible for the bulk production of a product or intermediate of interest in some systems, whereas stationary or post-exponential phase production can be obtained in other systems.

A classical batch culturing method is a closed system in which the media composition is set when the culture is started and is not altered during the culture process. That is, media is inoculated at the beginning of the culturing process with one or more microorganisms of choice and then is allowed to grow without adding additional microorganisms to the system. As used herein, a "batch" culture is in reference to not changing the amount of a particular carbon source initially added, whereas control of factors such as pH and oxygen and/or hydrogen concentration can be monitored and altered during the culture. In batch systems, metabolite and biomass compositions of the system change constantly up to the time the culture is terminated. Within batch cultures, cells (e.g., bacteria such as methylotrophs) will generally move from a static lag phase to a high growth logarithmic phase to a stationary phase where growth rate is reduced or stopped (and will eventually lead to cell death if conditions do not change).

A fed-batch system is a variation on the standard batch system in which a carbon substrate of interest is added in increments as the culture progresses. Fed-batch systems are useful when cell metabolism is likely to be inhibited by catabolite repression and when it is desirable to have limited amounts of substrate in the media. Since it is difficult to measure actual substrate concentration in fed-batch systems, an estimate is made based on changes of measurable factors such as pH, dissolved oxygen, and the partial pressure of waste gases. Batch and fed-batch culturing methods are common and known in the art (see, e.g., Thomas D. Brock, Biotechnology: A Textbook of Industrial Microbiology, 2nd Ed. (1989) Sinauer Associates, Inc., Sunderland, MA; Deshpande, 1992, Appl. Biochem. Biotechnol. 36:227).

Continuous cultures are "open" systems in the sense that defined culture media is continuously added to a bioreactor while an equal amount of used ("conditioned") media is removed simultaneously for processing. Continuous cultures generally maintain the cells at a constant high, liquid phase density where cells are primarily in logarithmic growth phase. Alternatively, continuous culture may be practiced with immobilized cells (e.g., biofilm) where carbon and nutrients are continuously added and valuable products, byproducts, and waste products are continuously removed from the cell mass. Cell immobilization may be achieved with a wide range of solid supports composed of natural materials, synthetic materials, or a combination thereof.

Continuous or semi-continuous culture allows for the modulation of one or more factors that affect cell growth or end product concentration. For example, one method may maintain a limited nutrient at a fixed rate (e.g., carbon source, nitrogen) and allow all other parameters to change over time. In other embodiments, several factors affecting growth may be continuously altered while cell concentration, as measured by media turbidity, is kept constant. The goal of a continuous culture system is to maintain steady state growth conditions while balancing cell loss due to media being drawn off against the cell growth rate. Methods of modulating nutrients and growth factors for continuous culture processes and techniques for maximizing the rate of product formation are well known in the art (see Brock, 1992).

In certain embodiments, culture media includes a carbon substrate as a source of energy for a $C_1$ metabolizing microorganism. Suitable substrates include $C_1$ substrates, such as methane, methanol, formaldehyde, formic acid (formate), carbon monoxide, carbon dioxide, methylated amines (methylamine, dimethylamine, trimethylamine, etc.), methylated thiols, or methyl halogens (bromomethane, chloromethane, iodomethane, dichloromethane, etc.). In certain embodiments, culture media may comprise a single $C_1$ substrate as the sole carbon source for a $C_1$ metabolizing microorganism, or may comprise a mixture of two or more $C_1$ substrates (mixed $C_1$ substrate composition) as multiple carbon sources for a $C_1$ metabolizing microorganism.

Additionally, some $C_1$ metabolizing organisms are known to utilize non-$C_1$ substrates, such as sugar, glucosamine or a variety of amino acids for metabolic activity. For example, some *Candida* species can metabolize alanine or oleic acid (Sulter et al., Arch. Microbiol. 153:485-489, 1990). *Methylobacterium extorquens* AM1 is capable of growth on a limited number of $C_2$, $C_3$, and $C_4$ substrates (Van Dien et al., Microbiol. 149:601-609, 2003). Alternatively, a $C_1$ metabolizing microorganism may be a recombinant variant having the ability to utilize alternative carbon substrates. Hence, it is contemplated that a carbon source in culture media may comprise a mixture of carbon substrates, with single and multi-carbon compounds, depending on the $C_1$ metabolizing microorganism selected.

In certain embodiments, the instant disclosure provides a method for making fuel, comprising converting biomass from a culture primarily comprising a $C_1$ metabolizing non-photosynthetic microorganism into an oil composition and refining the oil composition into a fuel. In certain embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In further embodiments, the oil composition is derived or extracted from cell membrane of the $C_1$ metabolizing non-photosynthetic microorganism, such as a methylotroph or methanotroph.

In certain embodiments, the instant disclosure provides a method for making fuel by refining an oil composition in a refining unit to produce fuel, wherein the oil composition is derived from a $C_1$ metabolizing non-photosynthetic microorganism, such as a methylotroph or methanotroph. In further embodiments, the method further comprises use of a processing unit for extracting the oil composition from the $C_1$ metabolizing non-photosynthetic microorganism. In still further embodiments, the method comprises (a) culturing $C_1$ metabolizing bacteria in the presence of a feedstock comprising a $C_1$ substrate in a controlled culturing unit, wherein the cultured bacteria produces an oil composition; (b) extracting the oil composition from the cultured bacteria in a processing unit; and (c) refining the extracted oil composition in a refining unit to produce fuel. In certain embodiments, the feedstock $C_1$ substrate is methane, methanol, formaldehyde, formic acid, carbon monoxide, carbon dioxide, a methylamine, a methylthiol, or a methylhalogen.

In certain embodiments, the instant disclosure provides a method for making natural products, such as ethanol, acetate, butanol, single-cell protein, sugars, or other metabolites or cellular products wherein the natural product is derived from a $C_1$ metabolizing non-photosynthetic microorganism, such as a methylotroph or methanotroph.

In further embodiments, the method further comprises use of a processing unit for extracting the natural product from the $C_1$ metabolizing non-photosynthetic microorganism.

In still further embodiments, the method comprises (a) culturing $C_1$ metabolizing bacteria in the presence of a feedstock comprising a $C_1$ substrate in a controlled culturing unit, wherein the cultured bacteria produce a natural product; (b) extracting the natural product from the cultured bacteria in a processing unit; and (c) refining the natural product to produce a commercial product. In certain embodiments, the feedstock $C_1$ substrate is methane, methanol, formaldehyde, formic acid, carbon monoxide, carbon dioxide, a methylamine, a methylthiol, or a methylhalogen.

In certain embodiments, the instant disclosure provides a method for making natural or non-natural products, such as ethanol, acetate, butanol, isoprene, propylene, farnesene, enzymes, or other metabolites or cellular products wherein the product is derived from a genetically engineered $C_1$ metabolizing non-photosynthetic microorganism, such as a methylotroph or methanotroph which has been transformed with a heterologous nucleotide sequence. In further embodiments, the method further comprises use of a processing unit for extracting the product from the genetically engineered $C_1$ metabolizing non-photosynthetic microorganism. In still further embodiments, the method comprises (a) culturing genetically engineered $C_1$ metabolizing bacteria in the presence of a feedstock comprising a $C_1$ substrate in a controlled culturing unit, wherein the cultured bacteria produce a natural product; (b) extracting the natural product from the cultured bacteria in a processing unit; and (c) refining the natural product to produce a commercial product. In certain embodiments, the feedstock $C_1$ substrate is methane, methanol, formaldehyde, formic acid, carbon monoxide, carbon dioxide, a methylamine, a methylthiol, or a methylhalogen.

In certain embodiments, the instant disclosure provides a method for making natural or non-natural products, such as ethanol, acetate, butanol, isoprene, propylene, farnesene, enzymes, or other metabolites or cellular products wherein the product is derived from a non-$C_1$ metabolizing microorganism, such as *Escherichia coli, Saccaromyces cerevisiae*, or other common production microorganism. In certain embodiments, the feedstock substrate is glucose, sucrose, glycerol, cellulose or other multicarbon feedstocks.

A loop reactor illustrated in FIG. 1 of U.S. Pat. No. 7,579,163 is described as including a substantially vertical downflow zone 3 and a substantially vertical upflow zone 5 separated by a substantially horizontal zone 4 which begins at the bottom of the substantially vertical downflow zone 3 and ends at the beginning of substantially vertical upflow zone 5. The presence of the substantially vertical downflow zone 3 and the substantially vertical upflow zone 5 results in a vertical distance between the gas liquid surface 22 at the end of outflow zone 6 and the centerline of the loop reactor in the horizontal zone 4. The '163 patent describes that this vertical distance is at least 10 meters or about 32.8 feet. The distance liquid medium flows upward through vertical upflow section 5 to a location where it enters horizontal effluent gas/liquid reaction medium separation section 6 depends on the rise in the substantially horizontal section 4 of loop and the rise in the substantially horizontal effluent gas/liquid reaction medium separation section 6. The presence of a substantially vertical downflow zone and a substantially vertical upflow zone of sufficient length to accommodate a vertical distance between the gas liquid surface at the end of an outflow zone 6 and the centerline of the loop reactor in the horizontal zone 4 on the order of 10 meters contributes significantly to the overall cost of designing and manufacturing a loop reactor with these zones. For example, the costs associated with designing and manufacturing structures required to physically support downflow and upflow vertical zones tall enough to accommodate vertical distances between the gas liquid surface 22 at the end of outflow zone 6 and the centerline of the loop reactor in the horizontal zone 4 on the order of 10 meters contributes significantly to the overall cost of designing, building and maintaining a loop reactor including such zones. Loop reactors with upflow and downflow vertical zones on the order of 10 meters tall require buildings in which such reactors are housed to have sufficient vertical clearance to accommodate such tall vertical upflow and downflow zones. A loop reactor of the type described in the '163 patent which includes a vertical distance between the gas liquid surface 22 at the end of outflow zone 6 and the centerline of the loop reactor in the horizontal zone 4 of at least 10 meters exhibits a static head or hydrostatic pressure in the substantially vertical downflow zone which is represented by the formula P=ρ g h, wherein P is the hydrostatic pressure in pascals, p is the fluid density in $kg/m^3$, g is the gravitational acceleration in $m/s^2$ and h is the length in meters of the vertical distance between the gas liquid surface 22 at the end of outflow zone 6 and the centerline of the loop reactor in the horizontal zone 4. For a loop reactor of the type described in the '163 patent which includes a vertical distance between the gas liquid surface 22 at the end of outflow zone 6 and the centerline of the loop reactor in the horizontal zone 4 of at least 10 meters, the hydrostatic pressure P at the bottom of the substantially vertical downflow zone 6 can be characterized as being at least 10 ρ g. The pressure on the inlet side of propeller 10 is the sum of this hydrostatic pressure P and the pressure in the effluent gas removal zone/top unit 2.

Figure 2:
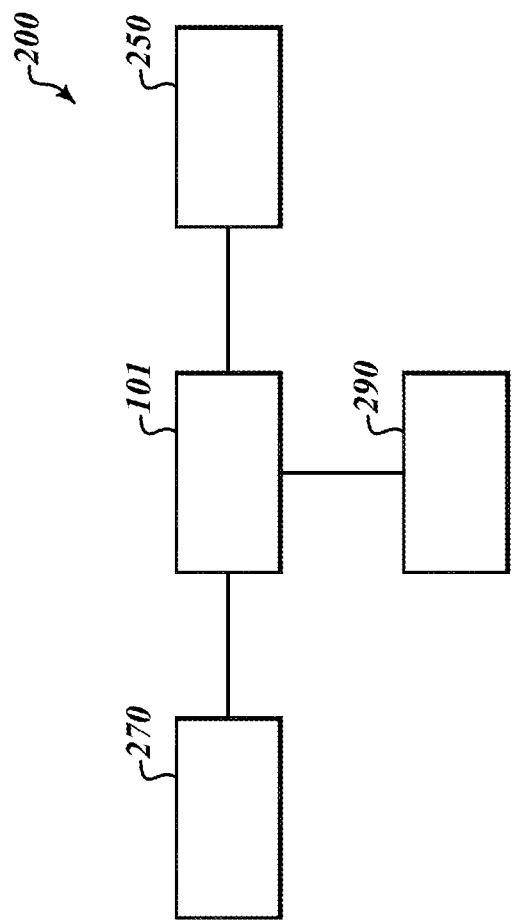
FIG. 2 shows a schematic block diagram of an example of a loop reactor for stimulating production of biomass and optional subsystems according to one or more illustrated and described embodiments.

FIG. 2 shows an exemplary system 200 for stimulating production of biomass that includes a loop reactor 101 along with a separation subsystem 250, an optional thermal subsystem 270 and optional control subsystem 290. Although shown as an integrated system 200, the optional subsystems may be installed or otherwise combined with the loop reactor 101 either individually or in any combination. One or more liquids and one or more gas substrates are introduced to the loop reactor 101 to form a multi-phase mixture with a liquid culture media that travels through the loop reactor 101. After passage through the loop reactor 101, the multi-phase mixture may contain one or more compounds produced by the biological organisms within the loop reactor 101, unconsumed nutrients and other compounds in the liquid within the multi-phase mixture, unconsumed gases in the gas bubbles within the multi-phase mixture, and microbiological organisms in the form of biosolids. Excess microbiological organisms may be removed from the loop reactor 101 as biomass either intermittently or continuously. Biomass accumulations within the loop reactor 101 may be removed to maintain the overall biomass within the loop reactor 101 within a defined range or above or below a defined threshold. In at least some instances, biomass removed from the loop reactor 101 may include one or more useful compounds. For example, the biological organisms within the excess biomass may contain an amount of one or more intracellular lipids or similar compounds useful in the production of a biofuel such as biodiesel or protein-containing products.

The one or more liquids may include any liquid suitable for sustaining or delivering one or more nutrients to the microbiological organisms within the loop reactor 101. Such liquids may include, but are not limited to, solutions containing water, one or more alcohols, minerals, one or more nitrogen-containing compounds, one or more phosphorus-containing compounds, and the like. In at least some instances, one or more fluid movers are used to deliver the one or more liquids to the loop reactor 101 in a controlled manner and pressure. The one or more fluid movers can include any type of pump or similar device capable of transferring a liquid between two points. Example fluid movers include, but are not limited to, centrifugal pumps, positive displacement pumps, progressing cavity pumps, double diaphragm pumps, and the like. Other illustrative fluid movers include, but are not limited to eductors, ejectors, and similar devices. The transfer of liquid to the loop reactor 101 can be flow controlled, pressure controlled, or controlled using combinations of pressure, temperature, flow, level, flowrate, superficial velocity, or compositional analysis process variable data gathered from one or more points within the loop reactor 101 or from one or more points within the system 200. In at least some instances, the transfer of liquid by the fluid mover can be controlled based on the measured concentration of one or more components or compounds (e.g., one or more carbon-containing or nitrogen-containing nutrients) within the loop reactor 101; for example, the flow of liquid transferred by the fluid mover may be increased in response to a measured decrease in nutrient concentration within the loop reactor 101.

The one or more gas substrates can include any gas, gases, or combination of gases suitable for sustaining or delivering one or more nutrients to the biological organisms within the loop reactor 101. Such gases can include, but are not limited to, one or more gases containing carbon compounds. Such gases can include, but are not limited to, one or more gases containing $C_1$ carbon compounds such as methane or carbon monoxide. The one or more gas substrates may also include one or more gases used in the metabolic processes of the biological organisms within the loop reactor 101. Such gases can include, but are not limited to, oxygen, oxygen-containing compounds and hydrogen. The one or more gas substrates may be transferred to the loop reactor 101 as a pure gas or as a gas mixture (e.g., syngas, a mixture of carbon monoxide and hydrogen). The one or more gas substrates may be transferred to the loop reactor 101 individually (e.g., methane and an oxygen-containing gas such as air may be transferred individually to minimize the likelihood of formation of an explosive gas mixture external to the loop reactor 101).

The one or more gas substrates may optionally be transferred to the loop reactor 101 using a gas mover. Example gas movers include, but are not limited to, rotary lobe compressors, centrifugal compressors, screw compressors, and the like. The delivery pressure of the one or more gas substrates depends upon a variety of factors including the operating pressure of the loop reactor 101 and the pressure drop associated with the gas distributor used to distribute the one or more gas substrates within the loop reactor 101. Similarly, the delivery flowrate of the one or more gas substrates may be manually or automatically controlled to maintain the concentration or level of dissolved gas within the loop reactor 101 within a defined range (e.g., dissolved oxygen above at least 4 ppm) based at least in part on the needs of the biological organisms present in the loop reactor 101. In at least some instances, the one or more gas substrates can be delivered to the loop reactor 101 at a pressure of from about 1.5 psig to about 600 psig, about 5 psig to about 600 psig; from about 25 psig to about 400 psig; or from about 50 psig to about 300 psig.

Any number of gases may be introduced through a common gas distribution header or any number of individual gas distribution headers. Such gas distribution headers may introduce all of the gas substrate at a single point within the loop reactor 101 or may introduce portions of the gas substrate at various locations throughout the loop reactor 101. In at least some instances, the gas substrate can include, but is not limited to, methane, carbon monoxide, hydrogen, or oxygen. In at least some instances, the feed rate of the gas substrate can be referenced to the feed rate of the liquid media. For example, methane may be introduced as a gas substrate at a rate of from about 0.1 grams of methane/liter of liquid media (g/l) to about 100 g/l; from about 0.5 g/l to about 50 g/l; or from about 1 g/l to about 25 g/l. Carbon monoxide ("CO") may be introduced as a gas substrate 204 at a rate of from about 0.1 grams of CO/liter of liquid media (g/l) to about 100 g/l; from about 0.5 g/l to about 50 g/l; or from about 1 g/l to about 25 g/l. Oxygen may be introduced as a gas substrate 204 at a rate of from about 1 grams of oxygen/liter of liquid media (g/l) to about 100 g/l; from about 2 g/l to about 50 g/l; or from about 5 g/l to about 25 g/l. Hydrogen may be introduced as a gas substrate 204 at a rate of from about 0.01 grams of hydrogen/liter of liquid media (g/l) to about 50 g/l; from about 0.1 g/l to about 25 g/l; or from about 1 g/l to about 10 g/l.

Within the loop reactor 101 the microbiological organisms will metabolize at least a portion of the carbon-containing compounds present in the multi-phase mixture. At least a portion of this process may include the production of additional microbiological organisms that increase the overall quantity of biomass present in the loop reactor 101. Left uncontrolled, the biomass within the loop reactor 101 may accumulate to a point such that one or more operational aspects of the loop reactor 101 (e.g., flowrate, pressure drop, production of desired products, etc.) is compromised or adversely affected by the presence of the excess biomass. In such instances, the ability to remove at least a portion of the biomass present in the loop reactor 101 is desirable. In at least some instances, biomass preferentially accumulates at a location within a gas/liquid separation vessel (102 in FIGS. 3 and 4) facilitating biosolids removal from the loop reactor 101 via the at least one biomass removal port (128 in FIGS. 3 and 4). The removed biomass can be delivered to separation subsystem 250 where the biomass can be further processed and desirable products recovered from the biomass.

In at least some instances, all or a portion of the biomass production process may be at least partially automatically controlled using a control subsystem 290. The control subsystem 290 may collect process-related information provided by one or more process elements in the form of signals containing analog or digital data representing one or more process variables. For instance, the control subsystem can collect process-related signals using one or more process elements including, but not limited to, mass flow sensors, volumetric flow sensors, temperature sensors, pressure sensors, level sensors, analytical sensors (e.g., dissolved oxygen sensors, biological oxygen demand or "BOD" sensors, pH sensors, conductivity sensors, and the like) or any other device capable of providing a signal containing data representative of one or more process-related conditions within the loop reactor 101.

The control subsystem 290 may execute one or more sets of instructions controlling, altering, or adjusting one or more aspects of the fermentation process based at least in part on the process variable signals received from the process elements. Such instructions may result in the generation of one or more control output signals by the control subsystem 290. The control output signals can be transmitted from the control subsystem 290 to one or more final control elements such as block valves, control valves, motors, variable speed drives, etc. The interaction between the final control elements and the fermentation process can, in turn, provide the control subsystem 290 with a high degree of relatively accurate control of the biomass production process.

For example, responsive to the receipt of one or more signals containing data indicative of the temperature of the multi-phase mixture in the loop reactor 101, the control subsystem 290 may initiate, alter, or cease the flow of thermal transfer media to a heat transfer unit operation. Similarly, responsive to the receipt of one or more signals containing data indicative of the dissolved oxygen level of the multi-phase mixture in the loop reactor 101, the control subsystem 290 may increase, decrease, or maintain the flow of the oxygen-containing gas substrate to the loop reactor 101. Although only two illustrative examples are provided herein, any flow, level, pressure, analytical value, or the like that is appropriate to the fermentation process may be similarly controlled by the control subsystem 290 using one or more appropriate process sensors and one or more appropriate final control elements.

Figure 3:
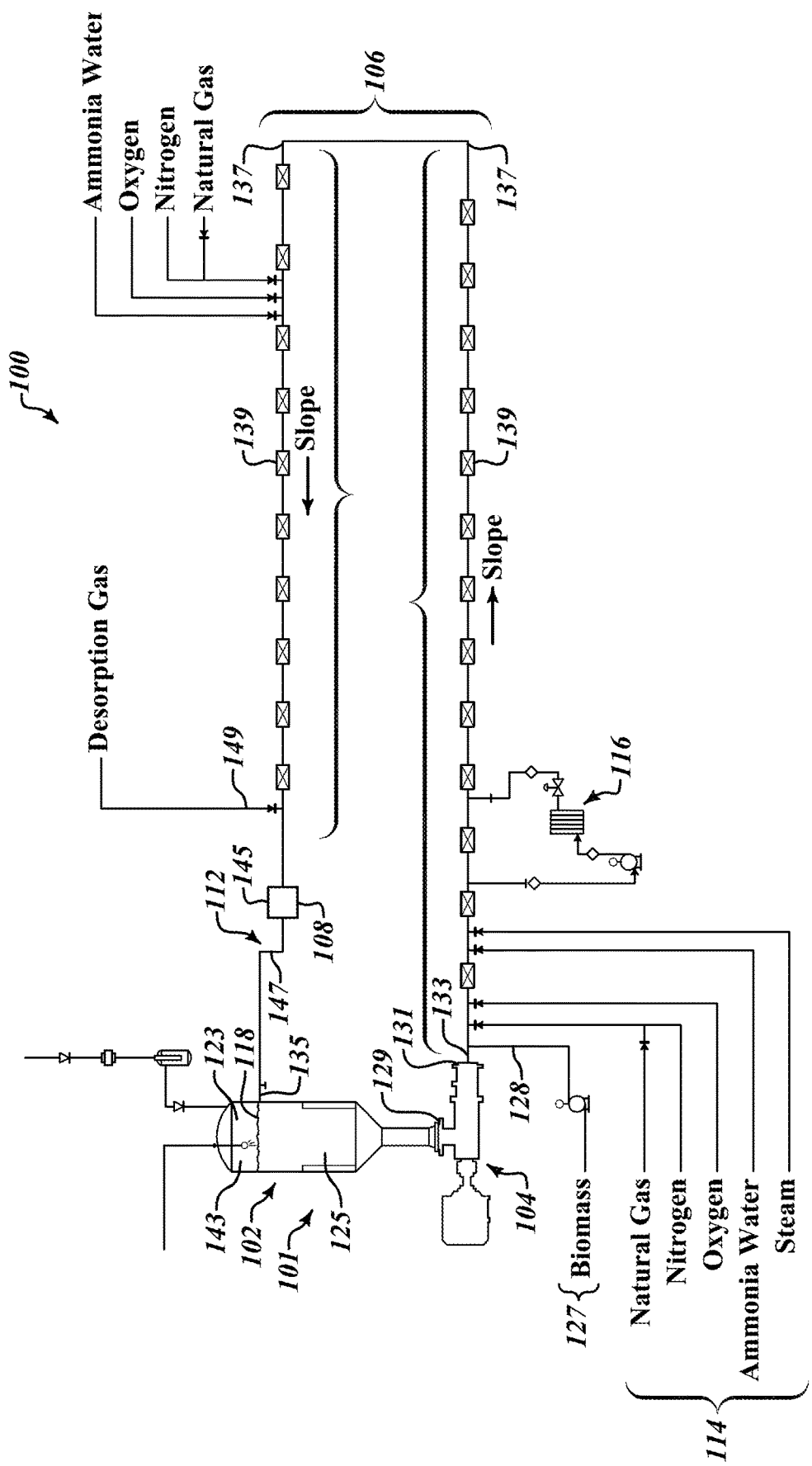
FIG. 3 shows a schematic view of an example system for stimulating production of biomass that is useful in fermenting a gaseous substrate that includes a first pressure reduction zone and a second pressure reduction zone according to one or more illustrated and/or described embodiments.
Figure 4:
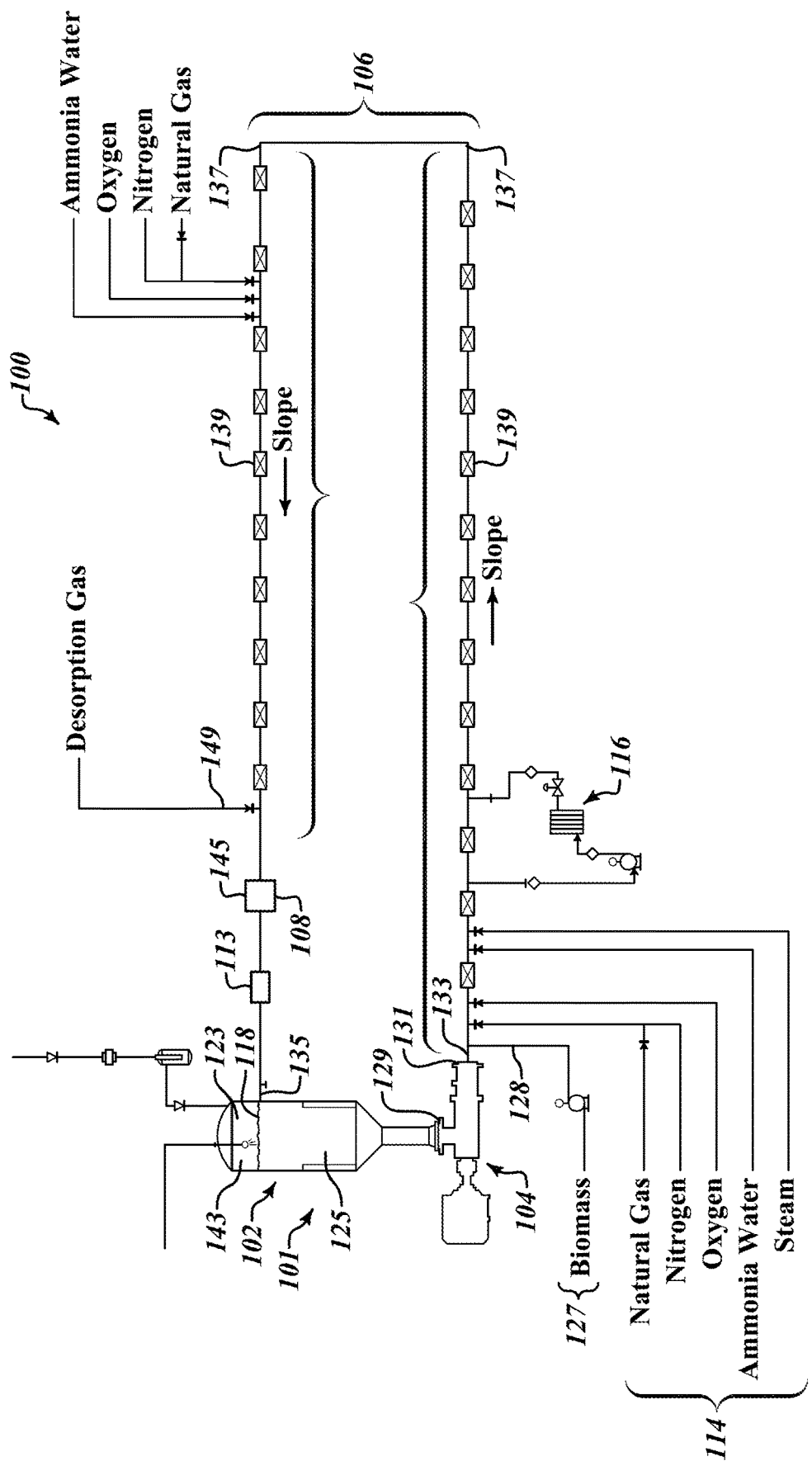
FIG. 4 shows a schematic view of an example system for stimulating production of biomass that is useful in fermenting a gaseous substrate that includes a first pressure reduction zone according to one or more illustrated and/or described embodiments.

FIGS. 3 and 4 show an exemplary system 100 for stimulating production of biomass. Exemplary system 100 includes a loop reactor 101 including a gas/liquid separation unit operation 102 (e.g., a gas/liquid separation vessel or other equipment capable of separating liquids and gases from a multi-phase mixture of liquid culture media including microorganisms and a fluid flow unit operation 104 (e.g., pump or other device capable of causing a fluid to move), a loop section 106 and a first non-vertical pressure reduction zone 108. As used herein, the loop section 106 refers to that portion of loop reactor 101 extending from the outlet of fluid flow unit operation 104 to the gas/liquid separation unit operation 102. Loop section 106 may or may not include vertical portions. When loop section 106 does not include vertical portions, it can be referred to as a non-vertical loop section 106. In additional embodiments of the exemplary system 100, loop reactor 101 includes a second pressure reduction zone 112 (illustrated in FIG. 3) downstream of the first non-vertical pressure reduction zone 108. In additional exemplary embodiments, second pressure reduction zone 112 may be a second non-vertical pressure reduction zone or it may be a vertical pressure reduction zone. A vertical pressure reduction zone 147 is illustrated in FIG. 3. Exemplary system 100 in additional embodiments includes other subsystems, including nutrient and/or mineral supply subsystem 114 and heat transfer unit operation(s) 116. Exemplary system 100 stimulates production of biomass by introducing gaseous substrate(s) and nutrient(s) to a liquid culture medium to form a multi-phase mixture of the liquid culture medium, supplied gaseous substrate(s) and nutrient(s). This multi-phase mixture flows through loop reactor 101 by the action of fluid flow unit operation 104. The liquid culture medium includes microorganisms capable of converting gaseous substrates to desirable products, some of which may be recovered from the microorganisms or from the gas phase and/or liquid phase that form in gas/liquid separation unit operation 102. Gaseous substrate(s) and nutrient(s) can be delivered to loop reactor 101 from nutrient supply subsystem 114, and loop reactor 101 is operated under conditions that promote mass transfer of gaseous substrate(s) and nutrient(s) into the liquid culture medium and into the microorganisms. Nutrients and minerals can be introduced at locations other than as indicated by nutrient/mineral supply subsystem 114. For example, minerals and/or nutrients may be supplied at heat transfer unit operation(s) 116. Gas/liquid separation vessel 102 receives the liquid culture medium, including any gases that remain in the liquid culture medium, and gases which have separated from the liquid culture medium, and separates them into a liquid phase and a gas phase. The liquid phase separated from the gas phase in gas/liquid separation vessel 102 is removed from gas/liquid separation vessel 102 and received by fluid flow unit operation 104.

Exemplary system 100 illustrated in FIG. 4 includes a loop section 106 that does not include any vertical sections. Exemplary system 100 illustrated in FIG. 3 includes a loop section 106 that includes a vertical section shorter than vertical sections included in loop sections of conventional loop reactors. For example, loop section 106 of exemplary system 100 in FIG. 3 can include a vertical section that is no more than 50%, no more than 40%, no more than 30%, no more than 20% or no more than 10% of the vertical distance between centerline of loop section 106 at its outlet 135 (i.e., at the inlet to the gas/liquid separation unit operation 102) and the centerline of loop section 106 at the outlet 131 of fluid flow unit operation 104. Referring to FIGS. 3 and 4, the portion of the loop reactor between the gas/liquid interface 118 within gas/liquid separation unit operation 102 and the centerline of loop section 106 at outlet 131 of fluid flow unit operation 104 is a substantially vertical downflow zone. The vertical distance between the gas/liquid interface 118 in gas/liquid separation unit operation 102 and the centerline of loop section 106 at outlet 131 of fluid flow unit operation 104 is equal to the vertical distance between the loop section centerline of loop section 106 at its outlet 135 and the centerline of loop section 106 at outlet 131 of fluid flow unit operation 104 when the gas/liquid interface 118 in gas/liquid separation unit operation 102 coincides with (i.e., is at the same elevation as) the loop section centerline of loop section 106 at its outlet 135. In other embodiments, the gas/liquid interface 118 in gas/liquid separation unit operation 102 is below the loop section centerline of loop section 106 at its outlet 135 and does not coincide with the loop section centerline of loop section 106 at its outlet 135. In these embodiments, the vertical distance between the gas/liquid interface 118 in gas/liquid separation unit operation 102 and the centerline of loop section 106 at outlet 131 of fluid flow unit operation 104 is less than the vertical distance between the loop section centerline of loop section 106 at its outlet 135 and the centerline of loop section 106 at outlet 131 of fluid flow unit operation 104. Exemplary system 100 is characterized by a vertical distance between the centerline of loop section 106 at its outlet 135 (i.e., at the inlet to the gas/liquid separation unit operation 102) and the centerline of loop section 106 at outlet 131 of fluid flow unit operation 104 (and the centerline of fluid flow unit operation 104 when the centerline of fluid flow unit operation 104 is at the same elevation as the centerline of loop section 106 at outlet 131 of fluid flow unit operation 104) that is less than ten meters, less than nine meters, less than eight meters, less than seven meters, less than six meters, less than five meters, less than four meters, less than three meters, less than two meters, or less than one meter. In accordance with the above described embodiment, such loop reactors exhibit a static head or hydrostatic pressure upstream of fluid flow unit operation 104 at the inlet of the fluid flow unit operation which is represented by the formula $P=\rho g h$, wherein P is the hydrostatic pressure in pascals, p is the fluid density kg/m$^3$, g is the gravitational acceleration in m/s$^2$ and h is the length in meters of the vertical distance between the gas/liquid interface 118 in gas/liquid separation unit operation 102 and the centerline of loop section 106 at outlet 131 of fluid flow unit operation 104. For loop reactors in accordance with the above embodiments, which includes a vertical distance between the gas/liquid interface 118 in gas/liquid separation unit operation 102 and the centerline of loop section 106 at outlet 131 of fluid flow unit operation 104 that is less than 10 meters, the hydrostatic pressure P at the inlet of fluid flow unit operation 104 which is at substantially the same elevation as the centerline of loop section 106 at outlet 131 of fluid flow unit operation 104 can be characterized as being less than 10 ρg. The hydrostatic pressure P at the inlet of the fluid flow unit operation 104 where the vertical distance between the gas/liquid interface 118 in gas/liquid separation unit operation 102 and the centerline of loop section 106 at outlet 131 of fluid flow unit operation 104 is less than nine meters, less than eight meters, less than seven meters, less than six meters, less than five meters, less than four meters, less than three meters, less than two meters, or less than one meter long can be characterized as being less than 9 ρg, 8 ρg, 7 ρg, 6 ρg, 5 ρg, 4 ρg, 3 ρg, 2 ρ g or ρg, respectively. The pressure on the inlet side of fluid flow unit operation 104 is the sum of this hydrostatic pressure P and the pressure in the headspace of gas/liquid separation unit operation 102.

In those embodiments of exemplary system 100 where the gas/liquid interface 118 is below the loop section centerline of loop section 106 at its outlet and does not coincide with the loop section centerline of loop section 106 at its outlet 135 and the vertical distance between the gas/liquid interface 118 in gas/liquid separation unit operation 102 and the centerline of loop section 106 at outlet 131 of fluid flow unit operation 104 that is less than 10 meters, the hydrostatic pressure P at the inlet to the fluid flow unit operation 104 can be characterized as being less than 10 ρg. The hydrostatic pressure P at the inlet to the fluid flow unit operation 104 where the vertical distance between the gas/liquid interface 118 in gas/liquid separation unit operation 102 and the centerline of loop section 106 at outlet 131 of fluid flow unit operation 104 is less than nine meters, less than eight meters, less than seven meters, less than six meters, less than five meters, less than four meters, less than three meters, less than two meters, or less than one meter long can be characterized as being less than 9 ρg, 8 ρg, 7 ρg, 6 ρg, 5 ρg, 4 ρg, 3 ρg, 2 ρ g or ρg, respectively.

As noted above, the pressure on the inlet side of fluid flow unit operation 104 is the sum of hydrostatic pressure P and the pressure in the headspace of gas/liquid separation unit operation 102. In exemplary embodiments described herein, the pressure at the inlet of fluid flow unit operation 104 which is at substantially the same elevation as the centerline of loop section 106 at outlet 131 is less than 9 ρg+ pressure in the headspace of gas/liquid separation unit operation 102, 8 ρg+ pressure in the headspace of gas/liquid separation unit operation 102, 7 ρg+ pressure in the headspace of gas/liquid separation unit operation 102, 6 ρg+ pressure in the headspace of gas/liquid separation unit operation 102, 5 ρg+ pressure in the headspace of gas/liquid separation unit operation 102, 4 ρg+ pressure in the headspace of gas/liquid separation unit operation 102, 3 ρg+ pressure in the headspace of gas/liquid separation unit operation 102, 2 ρg+ pressure in the headspace of gas/liquid separation unit operation 102 or ρg+ pressure in the headspace of gas/liquid separation unit operation 102 for systems 100 where the vertical distance between the gas/liquid interface 118 in gas/liquid separation unit operation 102 and the centerline of loop section 106 at outlet 131 of fluid flow unit operation 104 is less than nine meters, less than eight meters, less than seven meters, less than six meters, less than five meters, less than four meters, less than three meters, less than two meters, or less than one meter, respectively. Exemplary pressure at the inlet to fluid flow unit operation 104 are less than 0.9 bar gauge, less than 0.8 bar gauge, less than 0.7 bar gauge, less than 0.6 bar gauge, less than 0.5 bar gauge, 0.4 bar gauge, less than 0.3 bars gauge, less than 0.2 bars gauge or less than 0.1 bars gauge. For example, pressure at the inlet to fluid flow unit operation 104 ranges from 0.55 bar gauge to 1.0 bar gauge, from 0.55 bar gauge to 0.8 bar gauge or from 0.55 bar gauge to 0.7 bar gauge.

Loop reactors 101 in accordance with embodiments described herein include ratios of the length of the loop section 106 to the vertical distance between the gas/liquid interface 118 in gas/liquid separation unit operation 102 and the centerline of loop section 106 at outlet 131 of fluid flow unit operation 104 that are between 20:1 to 60:1 or between 30:1 to 50:1. Loop reactors in accordance with embodiments described herein are not limited to loop reactors that include ratios of the length of the loop section 106 to the vertical distance between the gas/liquid interface 118 in gas/liquid separation unit operation 102 and the centerline of loop section 106 at outlet 131 of fluid flow unit operation 104 that are between 20:1 to 60:1 or between 30:1 to 50:1. Loop reactors in accordance with embodiments described herein can include ratios of the length of the loop section 106 to the vertical distance between the gas/liquid interface 118 in gas/liquid separation unit operation 102 and the centerline of loop section 106 at outlet 131 of fluid flow unit operation 104 that fall outside the ranges of between 20:1 to 60:1 or between 30:1 to 50:1. For example, loop reactors in accordance with embodiments described herein have ratios of the length of the loop section 106 to the vertical distance between the gas/liquid interface 118 in gas/liquid separation unit operation 102 and the centerline of loop section 106 at outlet 131 of fluid flow unit operation 104 that are less than 20:1 or greater than 60:1. For example loop reactors 101 in accordance with embodiments described herein can have ratios that are greater than 60:1, e.g., ratio up to 100:1 or more.

Elements of loop reactor 101 including but not limited to gas/liquid separation unit operation 102 (e.g., a gas/liquid separation vessel or other equipment capable of separating liquids and gases from a multi-phase mixture of liquids, gases and microorganisms), fluid flow unit operation 104 (e.g., pump or other device capable of causing a fluid to move), loop section 106 and first non-vertical pressure reduction zone 108 can be a metallic, non-metallic, or composite structure. For example, the elements can include one or more metallic materials such as 304, 304L, 316, or 316L stainless steels. In some instances, one or more coatings, layers, overlays, inserts, or other materials can be deposited on, applied to, joined with, or formed integral to all or a portion of the metallic, non-metallic or composite structures to beneficially or detrimentally affect the ability for microbiological organisms to attach thereto or to grow thereupon. For example, a coating inhibiting the growth or attachment of microbiological organisms may be deposited on or formed integral with the surfaces of the loop reactor 101 that are thermally conductively coupled to heat transfer unit operation 116. In another example, a coating that inhibits the growth or attachment of biological organisms may be deposited on or formed integral with portions of loop reactor 101 where it is desired to achieve removal of accumulated biomass more easily.

In at least some instances, the construction of elements of loop reactor 101 can include features that facilitate sterilization of all or a portion of the process contact surfaces. Such sterilization can be accomplished for example using steam sterilization, ultraviolet sterilization, chemical sterilization, or combinations thereof. In at least some instances, one or more non-metallic materials or one or more non-metallic coatings may be used within all or a portion of the interior or exterior of some or all of the elements of loop reactor 101. The use of such non-metallic materials may advantageously provide, for example, sterilizable surfaces that are capable of supporting or promoting biological growth.

Gas/liquid separation vessel 102 can include any number of devices, systems, or combinations thereof to separate the multi-phase mixture 121 into at least a gas effluent 123 and a liquid effluent 125 which operate on the same principles as gas/liquid separators used with conventional bioreactors. In at least some instances, biosolids present in the multi-phase mixture 121 may be separated into a solids-containing effluent. In at least some instances, at least a portion of the solids-containing effluent from the gas/liquid separation vessel 102 can be combined with the one or more liquids and the mixture returned to gas/liquid separation vessel or the loop section 106. In at least some instances, the gas/liquid separation vessel 102 can include one or more gas/liquid separators operating in parallel or series.

The gas/liquid separation vessel 102 can include one or more passive separators (e.g., one or more wet cyclones or the like) capable of separating the gas effluent 123 and the liquid effluent 125 from the multi-phase mixture 121. In at least some instances, the passive separator may also include a solids separation section to separate at least a portion of the biosolids present in the multi-phase mixture 121. In other instances, the gas/liquid separation vessel 102 can include one or more active separation devices (e.g., a three-phase rotary separator) capable of separating the gas effluent 123, the liquid effluent 125, and the solids-containing effluent from the multi-phase mixture 121.

In at least some instances, the gas effluent 123 may include a mixture of one or more gas substrates (e.g., methane or carbon monoxide) and one or more gaseous byproducts (e.g., carbon dioxide) generated as a byproduct by the biological organisms in the loop reactor 101. In at least some instances, the gas effluent 123 may be separated and at least a portion of the one or more gas substrates recycled (not shown) to the loop reactor 101, for example as a gas substrate. In at least some instances, the gas effluent 123 may include one or more useful compounds. For example, the gas effluent 123 may contain an amount of one or more gaseous $C_{2+}$ hydrocarbon compounds and compounds based thereupon having value as either a finished product or as a raw material in a subsequent process. Such useful compounds may be separated from the gas effluent 123 prior to recycling at least a portion of the gas effluent 123 to the loop reactor 101.

In at least some instances, the liquid effluent 125 will include a mixture containing one or more liquids, nutrients, and the like introduced to the loop reactor 101 by nutrient and/or mineral supply subsystem 114. In at least some instances, the liquid effluent 125 may be removed from the loop reactor and returned to the gas/liquid separation vessel 102 by spraying onto the surface of the multi-phase mixture in the gas/liquid separation vessel 102 in order to reduce foaming within gas/liquid separation vessel 102. Anti-foam agents may be added to the liquid effluent 125 sprayed into the gas/liquid separation vessel 102 or may be sprayed into the gas/liquid separation vessel 102 without the liquid effluent 125. In at least some instances, the liquid effluent 125 may include one or more useful compounds. For example, the liquid effluent 125 may contain an amount of one or more liquid $C_{2+}$ hydrocarbon compounds including, but not, limited to alcohols, ketones, glycols, and other compounds based thereupon having value as either a finished product or as a raw material in a subsequent process. Such useful hydrocarbon compounds may be separated from the liquid effluent 125.

In some instances, the reactor is used to produce natural or non-natural products, such as ethanol, acetate, butanol, isoprene, propylene, isoprene, enzymes, or other metabolites or cellular products wherein the product is derived from a microorganism. In such cases, the products may be present in either the gas effluent 123 or the liquid effluent 125 depending on the physical properties of the product.

In at least some instances, the bottom of gas/liquid separation vessel 102 can be shaped, formed, or configured to promote the accumulation of biological material 127 (i.e., "biosolids" or "biomass") at a desired location within vessel 102. For example, the bottom of gas/liquid separation vessel 102 can be conically shaped, dished, or sloped such that biosolids 127 settling to the bottom of vessel 102 preferentially collect in one or more predetermined locations. In the embodiment illustrated in FIG. 3, liquid effluent 125 and biosolids 127 can be removed from the bottom of gas/liquid separation vessel 102 and delivered to fluid flow unit operation 104, e.g., a pump. The liquid effluent 125 and biosolids 127 removed from gas/liquid separation vessel 102 can be received at inlet 129 of pump 104 and output from an outlet 131 of pump 104. Outlet 131 of pump 104 is in fluid communication with inlet 133 of loop section 106 of loop reactor 101. Suitable pumps for moving liquid effluent 125 and biosolids 127 include pumps capable of moving fluids (liquids or gases) and slurries, by mechanical action and which are able to produce desired flow rates in the substantial absence of shear forces detrimental to the biomass and/or cavitation. Avoiding cavitation is desirable because cavitation causes gaseous substrates and nutrients in the multi-phase mixture to come out of solution making them less accessible to the biomass. Examples of such type of pumps are centrifugal pumps, although pumps which are not centrifugal pumps may also be used. For example, positive displacement pumps, progressive cavity pumps, double diaphragm pumps, and the like can also be used. Devices other than pumps can also be used to move the multi-phase mixture, for example, propellers driven by a motor, such as the propellers and motors described in U.S. Pat. No. 7,579,163 can be used instead of or in combination with a pump.

In FIGS. 3 and 4, outlet 131 of fluid flow unit operation 104 is in fluid communication with an inlet 133 of loop section 106. Loop section 106 extends from its inlet 133 to an outlet 135 of loop section 106. Outlet 135 of loop section 106 is in fluid communication with gas/liquid separation vessel 102. Loop section 106 can be formed from piping made from materials that do not adversely affect reaction/fermentation processes carried out using loop reactor 101. For example, a loop section 106 can be formed from piping made from the materials described above for elements of loop reactor 101. The cross-sectional area of loop section 106 may be constant or the loop section 106 may include one or more sections that have different cross-sectional areas. Reference to the cross-sectional area of loop section 106 in the present disclosure does not include the cross-sectional area of gas/liquid separation vessel 102. The inner diameter of the loop section 106 may vary over a wide range. Exemplary diameters range from about 20 centimeters to 3 meters. Other exemplary diameters range from 25 centimeters to 2.5 meters. When loop section 106 includes sections of differing cross-sectional areas, the sections of loop section 106 having larger cross-sectional area have cross-sectional areas that are at most three times the cross-sectional area of the sections of loop section 106 having smaller cross-sectional areas. In other exemplary embodiments, sections of loop section 106 having larger cross-sectional area, have cross-sectional areas that are at most two times the cross-sectional area of the sections of loop section 106 having smaller cross-sectional areas. In yet other exemplary embodiments, sections of loop section 106 having larger cross-sectional area, have cross-sectional areas that are at most 0.5 times the cross-sectional area of sections of loop section 106 having smaller cross-sectional areas. The length of loop section 106 can vary depending upon a number of factors, including the desired length of time the multi-phase mixture 121 resides in loop section 106. The length of loop section 106 may also be determined based on other factors such as, but not limited to total reactor/liquid volume desired, total pressure drop across the loop, desired substrate utilization and yield. In exemplary embodiments, loop section 106 can vary in the length at its centerline from about 30 m to about 250 m, 40 m to about 200 m, 50 m to about 150 m and 60 to about 100 m.

The embodiments of loop section 106 illustrated in FIGS. 3 and 4 are U-shaped, including two elbows 137 that bend at 90° angles when viewed from above. Loop section 106 can take other shapes. For example, loop section 106 can include more than the two 90° elbows 137 or it can include more than one elbow that is less than 90°. In other embodiments, loop section 106 can include numerous elbows that are greater than 90° or less than 90°.

Outlet 135 of loop section 106 is elevated relative to inlet 133 of loop section 106. Loop section 106 accommodates for this difference in elevation between its inlet 133 and its outlet 135 by being sloped. The specific slope of the loop section 106 or portions of loop section 106 depend in part on the length of loop section 106, the vertical distance between the centerline of loop section 106 at its inlet 133 and the centerline of loop section 106 at its outlet 135, and whether loop section 106 includes a second pressure reduction zone 112 that is not horizontal. Loop section 106 can be sloped upward from its inlet 133 to its outlet 135 to accommodate for the change in elevation between inlet 133 and outlet 135. Alternatively, a portion of loop section 106 can be sloped downward and a portion of loop section 106 can be sloped upward. In such alternative embodiments, the portion of loop section 106 that is sloped upward accounts for the loss in elevation resulting from the presence of the downward sloped portion of loop section 106 and the difference in elevation between inlet 133 of loop section 106 and outlet 135 of loop section 106. For example, the portion of loop section 106 extending from its inlet 133 to the first 90° elbow 137 in FIGS. 3 and 4 can be sloped downward, and the portion of loop section 106 extending from the first or second elbow 137 can be sloped upward to outlet 135 of loop section 106.

In embodiments of loop reactor 101 that include a second pressure reduction zone 112 which is not horizontal and accounts for a portion of the elevation change from exit 131 of fluid flow unit operation 104 to outlet 135 of loop section 106, the amount of elevation change that must be provided by the balance of non-vertical loop section 106 (i.e., the portion of loop section 106 that is not vertical) is reduced. When a second pressure reduction zone 112 which accounts for a portion of the elevation change from exit 131 of fluid flow unit operation 104 to outlet 135 of loop section 106 is not present, the amount of the elevation change provided by the balance of the non-vertical loop section 106 is greater compared to when such second pressure reduction zone 112 is present. In exemplary embodiments of loop reactor 101 described herein, which include a second pressure reduction zone 112 which accounts for a portion of the elevation change from exit 131 of fluid flow unit operation 104 to outlet 135 of loop section 106, such second pressure reduction zone 112 accounts for no more than 90% of the elevation change from the centerline of loop section 106 at its inlet 133 to outlet 135 of loop section 106, for no more than 80% of the elevation change from the centerline of loop section 106 at its inlet 133 to outlet 135 of loop section 106, for no more than 70% of the elevation change from the centerline of loop section 106 at its inlet 133 to outlet 135 of loop section 106, for no more than 60% of the elevation change from the centerline of loop section 106 at its inlet 133 to outlet 135 of loop section 106, for no more than 50% of the elevation change from the centerline of loop section 106 at its inlet 133 to outlet 135 of loop section 106, no more than 40% of the elevation change from the centerline of loop section 106 at its inlet 133 to outlet 135 of loop section 106, no more than 30% of the elevation change the centerline of loop section 106 at its inlet 133 to outlet 135 of loop section 106, no more than 20% of the elevation change from the centerline of loop section 106 at its inlet 133 to outlet 135 of loop section 106, no more than 10% of the elevation change from the centerline of loop section 106 at its inlet 133 to outlet 135 of loop section 106 or no more than 5% of the elevation change from the centerline of loop section 106 at its inlet 133 to outlet 135 of loop section 106.

The exemplary embodiments illustrated in FIGS. 3 and 4 include a plurality of static mixers 139, positioned along the length of loop section 106. Benefits of the use of static mixers are described in U.S. Pat. No. 7,579,163 and include mixing of the nutrient gases into the multi-phase mixture. Exemplary types of static mixers are also described in the '163 patent. Static mixers that can be used in embodiments described are not limited to those described in the '163 patent. Static mixers other than those described in the '163 patent can be used in the embodiments described herein. For example, other types of static mixers are available from companies such as StaMixCo LLC of Brooklyn, New York and Sulzer Management Ltd. of Winterthur, Switzerland. In the exemplary embodiment illustrated in FIGS. 3 and 4, 50 static mixers 139 are schematically represented by 23 blocks. The static mixers 139 of the exemplary embodiment of FIGS. 3 and 4 can be provided at a density of about one mixer per three meters of the loop section 106 when the static mixer has a length of about 1 meter. In other words, in certain instances, static mixers are spaced apart by a distance about equal to 3 times the length of one of the static mixers. The number of static mixers is not limited to 50 nor is their density limited to one mixer per 3 meters of loop section 106. In accordance with embodiments described herein, fewer or greater numbers of static mixers can be provided and the static mixers may be provided at a lesser or greater density. The particular number of static mixers used and the density at which they are deployed will be determined in part based upon their contribution to mass transfer of gas into the liquid and microorganisms and/or the pressure drop produced by the static mixers.

Continuing to refer to FIGS. 3 and 4, in exemplary embodiments, system 100 includes a nutrient and/or mineral supply subsystem 114 for introducing nutrients and minerals into loop section 106 at one or more locations between the outlet 131 of fluid flow unit operation 104 and first non-vertical pressure reduction zone 108. Introducing nutrients and/or minerals upstream of the first non-vertical pressure reduction zone 104 results in the introduced nutrients and/or minerals being present in portions of the loop section where the microorganisms are more active and the demand for the nutrients and/or minerals is high. Compared to portions of the loop section upstream of the first non-vertical pressure reduction zone, the microorganisms activity downstream of the first non-vertical pressure reduction zone 104 is lower, thus making introduction of the nutrients and/or minerals between the first non-vertical pressure reduction zone 104 and gas/liquid separation vessel 102 less effective. Such nutrients include nutrients capable of supporting or transporting dissolved or suspended sustenance to biomass forming microbiological organisms in the multi-phase mixture within the loop reactor 101. In the embodiment illustrated in FIGS. 3 and 4, nutrients and minerals are introduced at two locations along loop section 106 between the outlet 131 of fluid flow unit operation 104 and first non-vertical pressure reduction zone 108; however, in accordance with other embodiments, nutrient and/or mineral supply subsystem 114 can introduce nutrients and minerals at different locations along loop section 106 and can introduce nutrients/minerals at fewer than two locations or more than two locations along loop section 106. Subsystem 114 provides gaseous substrates/nutrients for introduction into a liquid culture medium to form a multi-phase mixture of the liquid culture medium and supplied gaseous substrates/nutrients. Such gaseous substrates/nutrients can include a single gas or a combination of gases capable of supporting or providing sustenance or nutrients to the biomass producing biological organisms in the loop reactor 101. As illustrated in FIGS. 3 and 4, exemplary nutrients include natural gas, nitrogen, oxygen and ammonia water. A source of steam can be provided for thermal energy and cleaning purposes. Nutrients that can be supplied by nutrient subsystem 114 are not limited to natural gas, nitrogen, oxygen and ammonium water. Other nutrients/minerals, such as methane, syngas, water, phosphate (e.g., as phosphoric acid), nitrates, urea, magnesium, calcium, potassium, iron, copper, zinc, manganese, nickel, cobalt and molybdenum, typically used as sulfates, chlorides or nitrates can also be provided by nutrient subsystem 114.

In exemplary embodiments, system 100 includes a heat transfer unit operation 116 for introducing or removing thermal energy from the multi-phase mixture in loop section 106. Heat transfer unit operation 116 can introduce thermal energy to or remove thermal energy from the multi-phase mixture in the loop section 106 at one or more locations along loop section 106. In the embodiments illustrated in FIGS. 3 and 4, heat transfer unit operation 116 removes or introduces thermal energy at one location along loop section 106; however, thermal energy can be removed or introduced at more than one location along loop section 106. In at least some instances, the microbiological activity that occurs within the loop reactor 101 generates heat as a byproduct. Left uncontrolled, such heat can adversely affect the metabolism or health of the microbiological organisms within the loop reactor 101. Alternatively, microbiological organisms may also have a temperature below which the metabolism or health of the organism is adversely affected. As such, the biological organisms within the loop reactor 101 have a defined temperature range providing optimal growth and metabolic conditions. In at least some instances, the multi-phase mixture within the loop reactor 101 can be maintained at a temperature of about 130° F. or less; about 120° F. or less; about 110° F. or less; about 100° F. or less; about 95° F. or less; about 90° F. or less; about 85° F. or less; or about 80° F. or less using the heat transfer unit operation 116. In at least some instances, the multi-phase mixture within the loop reactor 101 can be maintained at a temperature of from about 55° F. to about 120° F.; about 60° F. to about 110° F.; about 110° F. to about 120° F.; about 100° F. to about 120° F.; about 65° F. to about 100° F.; about 65° F. to about 95° F.; or about 70° F. to about 90° F. using heat transfer unit operation 116.

In exemplary embodiments described herein, gas pressure in headspace 143 of gas/liquid separation unit operation 102 ranges from about 0.2 to about 0.6 bars gauge; however, the gas pressure in the headspace 143 is not limited to a range of about 0.2 to about 0.6 bars gauge. For example, in exemplary embodiments described herein, the gas pressure in headspace 143 can be less than 0.2 bars or greater than about 0.6 bars gauge. The pressure at outlet 131 of pump 104 ranges from about 2.5 bars to about 4.0 bars gauge; however, the pressure at outlet 131, of pump 104 is not limited to a range of about 2.5 bars to about 4.0 bars gauge. For example, in exemplary embodiments described herein, the pressure at outlet 131 of pump 104 can be less than about 2.5 bars or greater than about 4.0 bars gauge. In exemplary embodiments that include static mixers 139, the pressure drop across a static mixer ranges from about 0.03 to about 0.05 bars gauge; however, the pressure drop across a static mixer is not limited to a range from about 0.03 to about 0.05 bars gauge. For example, in exemplary embodiments described herein, the pressure drop across a static mixer may be less than 0.03 bars or greater than 0.05 bars gauge. In accordance with exemplary embodiments described herein, pressure within loop section 106 at the beginning of non-vertical pressure reduction zone 108 ranges from about 1.5 to about 2.5 bars gauge; however, the pressure within loop section 106 at the beginning of non-vertical pressure reduction zone 108 is not limited to a range from about 1.5 to about 2.5 bars gauge. For example, pressure within loop section 106 at the beginning of non-vertical pressure reduction zone 108 may be less than about 1.5 bars or greater than about 2.5 bars. In accordance with exemplary embodiments described herein, pressure within loop section 106 at the end of non-vertical pressure reduction zone 108 ranges from about 0.2 bars to about 0.6 bars gauge; however, the pressure within loop section 106 at the end of non-vertical pressure reduction zone 108 is not limited a range of about 0.2 bars to about 0.6 bars gauge. For example, in accordance with embodiments described herein, pressure within loop section 106 at the end of non-vertical pressure reduction zone 108 can be less than about 0.2 bars or greater than about 0.6 bars gauge. In embodiments described herein, the pressure drop across non-vertical pressure reduction zone 108 can range from about 1.2 bars to about 2.3 bars gauge; however, the pressure drop across the non-vertical pressure reduction zone 108 is not limited to a range from about 1.2 bars to about 2.3 bars gauge. For example, the pressure drop across the non-vertical pressure reduction zone 108 can be less than 1.2 bars or more than 2.3 bars gauge. In some instances, the pressure drop across non-vertical pressure reduction zone 108 accounts for at least 20%, at least 30%, at least 40%, at least 50%, at least 60%, at least 70% or at least 80% of the pressure drop between the outlet of fluid flow unit operation 104 and the headspace 143 of gas/liquid separation vessel 102. The foregoing description regarding pressure drops across non-vertical pressure reduction zone 108 and percentage of the pressure drop between the outlet of fluid flow unit operation 104 and headspace 143 of gas/liquid separation vessel 102 attributable to non-vertical pressure reduction zone 108 applies equally to the pressure drop across pressure reduction device 145 that is located in pressure reduction zone 108.

In embodiments illustrated in FIGS. 3 and 4, first non-vertical pressure reduction zone 108 is located downstream of the last static mixer 139 and upstream of the outlet 135 of loop section 106 which is in fluid communication with gas/liquid separation unit operation 102. First non-vertical pressure reduction zone 108 includes a pressure reduction device 145. In accordance with embodiments illustrated in FIGS. 3 and 4, the pressure within loop section 106 immediately downstream of pressure reduction device 145 is less than the pressure within loop section 106 immediately upstream of pressure reduction device 145. Pressure reduction device 145 causes the pressure within loop section 106 immediately downstream of pressure reduction device 145 to be less than the pressure within loop section 106 immediately upstream of pressure reduction device 145. Preferred devices for use as pressure reduction device 145 include devices that provide the desired reduction in pressure by means other than a change in hydrostatic pressure and without exposing the liquid culture media and microorganisms contained therein to forces resulting from shearing or cavitation that damage the microorganisms. For example, pressure reduction device 145 can be a flow control device, such as a control valve or a back pressure control valve (as opposed to a check valve) or an expansion joint (e.g., a pipe joint having an upstream diameter that is less than its downstream diameter) or a combination of multiple expansion joints or a combination of a control valve and one or more expansion joints. Exemplary control valves include control valves that are actuated hydraulically, pneumatically, manually, by a solenoid, or by a motor; however, control valves, useful in embodiments described herein, are not limited to the foregoing types of control valves. Likewise, pressure reduction device 145 is not limited to control valves and expansion joints and combinations thereof. For example, pressure reduction device 145 can be a device that is not a control valve or an expansion joint that results in the pressure within loop section 106 immediately downstream of the device being less than the pressure within loop section 106 immediately upstream of the device.

In accordance with embodiments described herein, pressure reduction device 145 can be a variable pressure reduction device, such as a control valve which can control media flow by varying the size of the flow passage, e.g., manually or based on a signal from a controller that is implementing a feedback control loop based on input from sensors which detect process parameters, such as pressure, temperature, gas concentration (e.g., oxygen, carbon dioxide, methane) pH, liquid media density circulation rate, biomass concentrations, or flow times between two points along the loop section 106. Employing a variable pressure reduction device allows for the difference in the pressure within loop section 106 immediately upstream of the device and the pressure within loop section 106 immediately downstream of the device to be adjusted by varying the degree to which the device is open. For example, the difference in the pressure can be decreased by opening the device and the difference pressure can be increased by closing the device. The ability to vary the pressure within the loop section 106 upstream of the variable pressure reduction device provides operators the ability to better control the processes occurring within loop section 106. For example, the variable pressure reduction device can be used to decrease the pressure within loop section 106 upstream of the variable pressure reduction device by opening (increasing the flow rate through) the variable pressure reduction device. Reducing the pressure within loop section 106 allows operators to slow down mass transfer, reduce production rates, reduce nutrient demands and increase rates of gas desorption from the multi-phase mixture. The variable pressure reduction device can be used to increase the pressure within loop section 106 upstream of the variable pressure reduction device by closing (reducing the flow rate through) the variable pressure reduction device. Increasing the pressure in loop section 106 allows operators to increase the mass transfer rate, increase production rate, increase nutrient demands and decrease rates of gas desorption from the multi-phase mixture.

Utilizing a variable pressure reduction device also provides operators with the ability to better control the pressure within loop section 106 downstream of the variable pressure reduction device. For example, utilizing the variable pressure reduction device to decrease the pressure within loop section 106 downstream of the variable pressure reduction device allows operators to promote the desorption of gases (e.g., carbon dioxide) which can inhibit the biological process occurring in the loop section. Utilizing the variable pressure reduction device to increase the pressure within loop section 106 downstream of the variable pressure reduction device allows operators to inhibit the desorption of gases (e.g., nutrient gases such as oxygen and methane) which are needed to fuel the biological processes occurring in the loop section 106. Inhibiting the desorption of gases such as oxygen and methane may be desired in order to manage the risk of combustion fueled by the oxygen and methane gas.

Figure 7A:
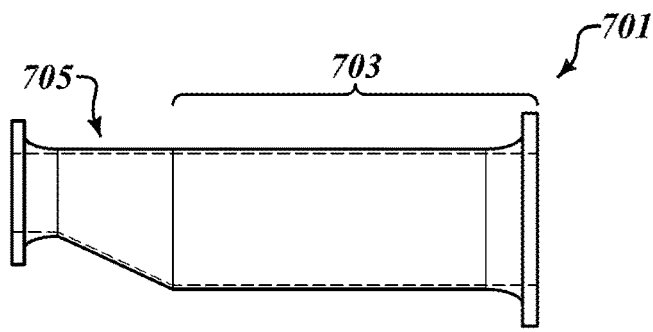
FIG. 7A is an elevational view a portion of a non-vertical pressure reduction device in accordance with one or more illustrated and/or described embodiments.
Figure 7B:
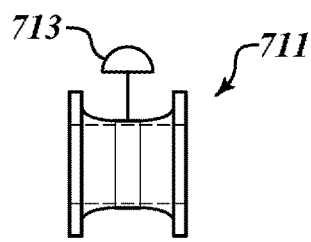
FIG. 7B is an elevational view of a portion of a non-vertical pressure reduction device in accordance with one or more illustrated and/or described embodiments.
Figure 7C:
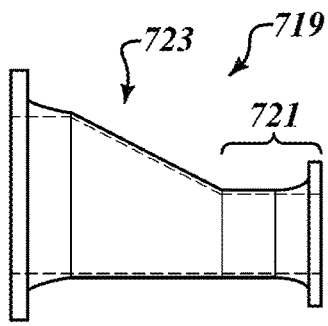
FIG. 7C is an elevational view of a portion of a non-vertical pressure reduction device in accordance with one or more illustrated and/or described embodiments.
Figure 7D:
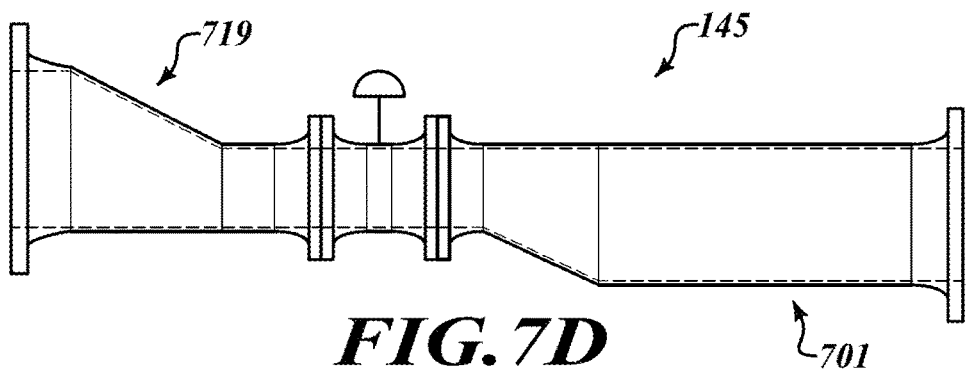
FIG. 7D is an elevational view of a non-vertical pressure reduction device formed by assembling the portions of a non-vertical pressure reduction device illustrated in FIGS. 7A, 7B and 7C.

Referring to FIG. 7D, an exemplary variable pressure reduction device 145 useful in the non-vertical pressure reduction zone 108 of loop reactors 100 in accordance with embodiments described herein is illustrated. One end of variable pressure reduction device 145 is attached to a portion of loop section 106 that is upstream of variable pressure reduction device 145. The other end of variable pressure reduction device 145 is attached to the portion of loop section 106 that is downstream of variable pressure reduction device 145. Referring to FIG. 7A, variable pressure reduction device 145 includes an eccentric reducer 701. Eccentric reducer 701 includes a pipe section 703 having a substantially constant inner diameter and an eccentric reducer section 705. The inner diameter of pipe section 703 is constant and is substantially the same as the inner diameter of the portion of loop section 106 to which pipe section 703 is attached. Eccentric reducer section 705 includes an end adjacent pipe section 703 which has an inner diameter that is equivalent to the inner diameter of pipe section 703. The smaller end of eccentric reducer 705 opposite the end adjacent to pipe section 703 has a smaller diameter. The diameter of the smaller end of eccentric pipe reducer 705 is equivalent to the diameter of the control valve 711 described below which is downstream of eccentric pipe reducer 705. Between the two ends of the eccentric reducer 705, the inner diameter transitions from the larger diameter end to the smaller diameter end and has an edge that is parallel to the portion of loop section 106 to which it is connected and the portion of the control valve 711 to which it is connected.

Referring to FIGS. 7A, 7B and 7D, variable pressure reduction device 145 includes a control valve 711 attached to the smaller end of eccentric reducer 701. Control valve 711 has an inner diameter that is substantially equivalent to the inner diameter of the smaller end of eccentric pipe reducer 705. Media flow through control valve 711 can be adjusted by varying the size of the flow passage within control valve 711 by manipulation of the handle 713 of control valve 711. As described above, handle 713 can be manipulated by an electronic controller.

Referring to FIGS. 7A, 7C and 7D, the end of variable pressure reduction device 145 opposite eccentric reducer 701 includes an eccentric expander 719. Eccentric expander 719 includes a pipe section 721 having a substantially constant inner diameter and an eccentric expander section 723. The inner diameter of pipe section 721 is constant and is substantially the same as the inner diameter of control valve 711 to which pipe section 721 is attached. Eccentric expander section 723 includes an end adjacent to pipe section 721 which has an inner diameter that is equivalent to the inner diameter of pipe section 721. The larger end of eccentric expander 723 opposite the end attached to pipe section 721 has an inner diameter that is substantially equivalent to the inner diameter of the portion of loop section 106 that is attached to the larger end of eccentric expander 723. In some embodiments, the inner diameter of the loop section 106 downstream of variable pressure reduction device 145 and the inner diameter of the end of eccentric expander 723 attached to a portion of loop section 106 that is downstream of eccentric expander 723 are larger than the diameter of the loop section 106 upstream of pressure reduction device 145. Between the two ends of the eccentric expander 719, the inner diameter transitions from the smaller diameter end to the larger diameter end and has an edge that is parallel to the portions of loop section 106 to which it is connected and an edge of the control valve 711 to which it is connected.

In accordance with other embodiments of variable pressure reduction device 145, one or both of eccentric reducer 701 and eccentric expander 723 are omitted. In such embodiments, one end of control valve 711 is attached to an end of loop section 106 that is upstream from control valve 711 and the other end of control valve 711 is attached to in in a loop section 106 that is downstream of control valve 711. Utilization of eccentric reducer 701 and eccentric expander 723 facilitate utilization of a control valve having an inner diameter that is smaller than the inner diameter of a control valve that would be needed if the eccentric reducer 701 and the eccentric expander 723 are not utilized. A control valve with a smaller inner diameter (compared to a similar control valve with a larger inner diameter) is able to control the pressure drop across the valve with more precision and greater sensitivity. Such precision and greater sensitivity may be preferred in some implementations.

Alternatives to a control valve 713 for use in pressure reduction device 145 include one or more expansion joints or concentric expanders which cause the pressure in loop section 106 downstream of the expansion joint/concentric expander to be reduced compared to the pressure in the loop section 106 upstream of the expansion joint/concentric expander.

In accordance with embodiments described herein and illustrated in FIG. 3, downstream of the first pressure reduction zone 108, loop section 106 can include a second pressure reduction zone 112. In embodiments illustrated in FIG. 3, second pressure reduction zone 112 is located downstream of the first pressure reduction zone 108 and upstream of the outlet 135 of loop section 106, which is in fluid communication with gas/liquid separation unit operation 102.

In the embodiment illustrated in FIG. 3, second pressure reduction zone 112 is provided by modifying loop section 106 to include a section that is oriented vertically. The vertical orientation of a section of loop section 106 provides a second pressure reduction zone 112 that results in the pressure within loop section 106 at the upper end of second pressure reduction zone 112 being less than the pressure within loop section 106 at the lower end of the second pressure reduction zone 112. The pressure reduction provided by second pressure reduction zone 112 is attributable, at least in part, to the difference in hydrostatic pressure from the top to the bottom of the second pressure reduction zone 112. The length of the vertical portion of second pressure reduction zone 112 can be determined at least in part based upon the desired reduction in pressure to be provided by second pressure reduction zone 112. For example, in exemplary embodiments, the length of the vertical portion of second pressure reduction zone 112 ranges from about 1 meter to less than about 10 meters; however, the length of the vertical portion of second pressure reduction zone 112 is not limited to a range from about 1 meter to less than about 10 meters. For example, the length of the vertical portion of the second pressure reduction device can be less than about 1 meter or greater than about 10 meters. Second pressure reduction zone 112 can also include a pressure reduction device 147 of the type described above with respect to first pressure reduction device 145. Utilizing a second pressure reduction zone 112 provides added flexibility in controlling the pressure within loop section 106 which can lead to greater precision in controlling the pressure which can lead to an improved process productivity and stability. In certain embodiments, the second pressure reduction zone 112 accounts for 60% or less, 50% or less, 40% or less, 30% or less, 20% or less or 10% or less of the length of the vertical distance between the gas/liquid interface 118 in gas/liquid separation unit operation 102 and the centerline of loop section 106 at outlet 131 of fluid flow unit operation 104.

Referring to the embodiments of FIG. 4, an optional second pressure reduction zone 113 can include a pressure reduction device of the type described above with respect to pressure reduction device 145. In accordance with embodiments of FIG. 4, second pressure reduction zone 113 is a non-vertical pressure reduction zone and includes a pressure reduction device. In exemplary embodiments, first pressure reduction device 145 of the first pressure reduction zone 108 is separated from the pressure reduction device of the second pressure reduction zone 113 by a non-vertical portion of the loop section 106. In accordance with embodiments illustrated in FIG. 4, the multi-phase mixture in loop section 106 flows from first non-vertical pressure reduction zone 108 to the gas/liquid separation unit operation 102 without flowing in a vertical direction. In accordance with embodiments according to FIG. 4, when a second pressure reduction zone 113 is present, it accounts for less of a pressure drop compared to the pressure drop across first pressure reduction zone 108. For example, the pressure drop across second pressure reduction zone 113 is about equal to the pressure difference between headspace 143 of gas/liquid separation vessel 102 and the pressure at the outlet of the first pressure reduction zone 108 and/or pressure reduction device 145. Such pressure drop across second pressure reduction zone 113 can range between about 0.1 bars to about 0.5 bars; however, the pressure drop across second pressure reduction zone 113 is not limited to a range between about 0.1 bars to about 0.5 bars. For example the pressure drop across second pressure reduction zone 113 can be less than 0.1 bars or greater than 0.5 bars. In some instances, the pressure drop across second pressure reduction zone 113 accounts for less than 10%, less than 5%, less than 3% or less than 2% of the pressure drop from the outlet of fluid flow unit operation 104 to the headspace 143 of gas/liquid separation vessel 102. The foregoing description regarding pressure drops across second pressure reduction zone 113 and percentage of the pressure drop from the outlet of fluid flow unit operation 104 to headspace 143 of gas/liquid separation vessel 102 attributable to pressure reduction zone 113 applies equally to the pressure drop across second pressure reduction device 147 in pressure reduction zone 112 of FIG. 3. Utilizing a second pressure reduction zone 113 provides added flexibility in controlling the pressure within loop section 106 which can lead to greater precision in controlling the pressure which can lead to improved process productivity and stability.

Loop section 106 upstream of first non-vertical pressure reduction zone 108 includes a desorption gas inlet 149. In the illustrated embodiment, desorption gas inlet 149 is in fluid communication with a source of desorption gas, e.g., nitrogen, and in fluid communication with a non-vertical section of loop section 106. Thus, in accordance with embodiments illustrated in FIGS. 3 and 4, desorption gas can be introduced into a non-vertical section of loop section 106. Introducing a desorption gas into the multi-phase mixture at desorption gas inlet 149 causes a decrease in the partial pressure of other gases present in the multi-phase mixture (e.g., carbon dioxide and methane). Reducing the partial pressure of other gases present in the multi-phase mixture can have the effect of reducing the mass transfer of nutrient gases into the microorganism and/or causing the other gases to come out of solution.

In an alternative embodiment, the desorption gas inlet 149 is located in a non-vertical section of loop section 106 between first pressure reduction zone 108 and outlet 135 of loop section 106. Providing the desorption gas inlet 149 at this location allows for the introduction of the desorption gas in a section of loop section 106 downstream of the first pressure reduction zone where the pressure has been reduced by passing the multiphase mixture through the first pressure reduction zone 108 and/or the second pressure reduction zone 112 in FIG. 3 or 113 in FIG. 4. As described in the previous paragraph, introduction of a desorption gas into the multi-phase mixture causes a decrease in the partial pressure of other gases present in the multi-phase mixture (e.g., carbon dioxide and methane). Reducing the partial pressure of other gases present in the multi-phase mixture can have the effect of reducing the mass transfer of nutrient gases into the microorganism and/or causing the other gases to come out of solution. Locating the desorption gas inlet 149 downstream of first pressure reduction zone 108, avoids introducing the desorption gas into the multi-phase mixture at a location where the desorption gas can affect the performance of the first pressure reduction zone 108 and/or second pressure reduction zones 112 or 113. For example, gas that separates from the multi-phase mixture can affect the performance of the first pressure reduction zone 108 in reducing the pressure. For example, if the first pressure reduction zone 108 includes a pressure reduction device in the form of a control valve, increasing amounts of gas desorbed from the multi-phase mixture can make it more difficult for the valve to control flow and pressure reduction. Introducing the desorption gas downstream of the first pressure reduction zone 108 avoids this problem.

Figure 5:
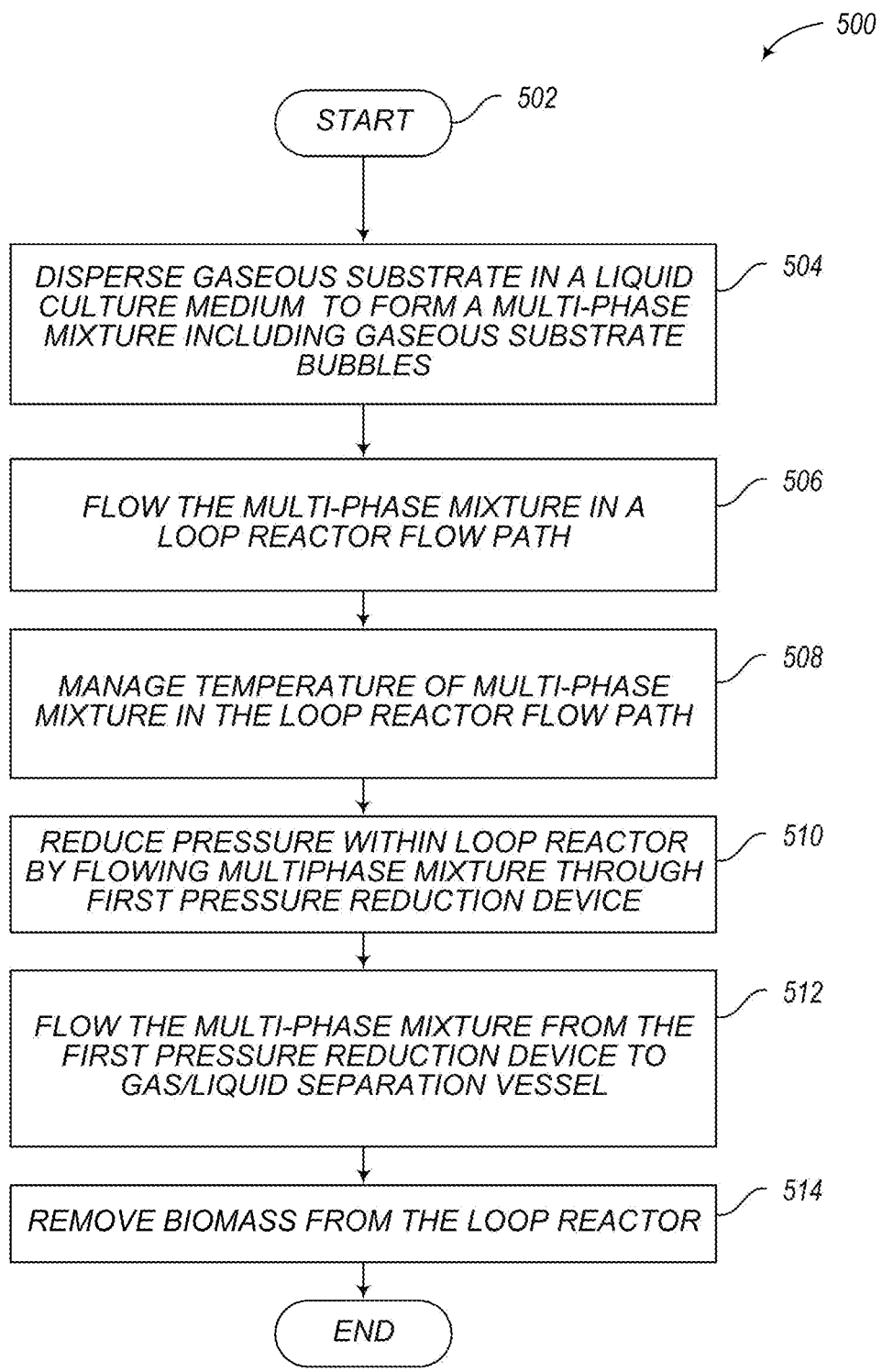
FIG. 5 shows a high level flow diagram of a fermentation process that includes flowing a multi-phase mixture through a first pressure reduction zone of a loop reactor, according to one or more illustrated and/or described embodiments.

FIG. 5 shows a high level method of operation 500 of a system 100 for stimulating production of biomass using one or more loop reactors 101 described in detail above with regard to FIGS. 2-4. Such systems advantageously introduce one or more gaseous substrates and a liquid media containing one or more nutrients into a liquid culture media containing at least one microorganism capable of utilizing the gaseous substrates and liquid nutrients to grow. The combination of the one or more gaseous substrates, liquid media containing one or more nutrients and liquid culture media containing at least one microorganism results in a multi-phase mixture that is circulated through a loop reactor 101. The conditions within the loop reactor 101 are controlled to promote mass transfer and subsequent microbiological uptake of the gaseous substrate and liquid nutrients, reduction of pressure within the loop reactor and desorption of gases from the multi-phase mixture. The multi-phase mixture after passing through the loop section 106 of the loop reactor 101 is received by a gas/liquid separation unit operation 102 where the multi-phase mixture is separated into liquid and gas phases. The method commences at 502.

At 504 a gaseous substrate is dispersed within the liquid media to form the multi-phase mixture. Such dispersion may occur at or near inlet 133 of loop section 106, although additional quantities of gaseous substrate may be introduced into the liquid culture media at other locations of loop section 106 and the liquid media at or near the inlet 133 of loop section 106 may already contain some dissolved gaseous substrates. In some instances, gaseous substrate may be dispersed at multiple points along loop section 106 and the gaseous substrate at each dispersion point may have the same or a different temperature, pressure, composition, or combinations thereof. The ability to vary physical or compositional properties of the gaseous substrate at different locations along the loop section 106 advantageously permits the tailoring of the gaseous substrate not only to the specific microbiological species present in the multi-phase mixture, but also to the specific location of the microbiological species within the loop section 106 based on the dispersion point of the gaseous substrate.

At 506 the multi-phase mixture is flowed through the loop section 106 of loop reactor 101. As the multi-phase mixture flows through the loop section 106, it contacts a plurality of static mixers 139, which promote the mixing of the gaseous substrate and/or nutrients into the liquid culture medium. By adjusting or otherwise controlling the flow rate of the multi-phase mixture through loop reactor 101, the length of time the bubbles of gaseous substrate and nutrients are in contact with the microorganism(s) can be modified. Increasing the length of time the bubbles of gaseous substrate and nutrients are in contact with the microorganism(s) can increase the amount of mass transfer of gaseous materials into the microorganisms and the microbiological uptake of gaseous materials by the microorganism. Conversely, decreasing the length of time the bubbles of gaseous substrate and nutrients are in contact with the microorganism(s) can decrease the amount of mass transfer of gaseous materials into the microorganisms and the microbiological uptake of gaseous materials by the microorganisms. In some instances, the length of time the bubbles of the gaseous substrate and nutrients are in contact with the microorganisms can be measured and controlled. For example, a control subsystem 290 can alter, adjust or control the fluid velocity of the multi-phase mixture through the loop reactor. In some instances, the temperature, pressure, or composition of the gaseous substrate may be altered, adjusted or controlled via the control subsystem 290 to maintain a desired gas substrate bubble size within loop reactor 106. In other instances, the temperature, pressure, or composition of the gas substrate may be altered, adjusted or controlled via the control subsystem 290 to maintain the concentration of one or more gas substrate components (e.g., methane, carbon dioxide, hydrogen, oxygen, nitrogen, etc.) within the liquid phase of the multi-phase mixture.

At 508 the temperature of the multi-phase mixture within loop reactor 101 can be altered, adjusted, or controlled to maintain the temperature within a defined temperature range. In at least some instances, the defined temperature range may be selected or otherwise chosen based at least in part on the microbiological species used within system 100. Excess heat may be generated as a byproduct by the microbiological organisms responsible for at least a portion of the activity within system 100. This excess heat, if left uncontrolled, could inhibit or adversely affect the growth or metabolism of some or all of the microbiological organisms within system 100. In at least some instances, cooling of the multi-phase mixture in loop reactor 101 may be provided to maintain the temperature of the multi-phase mixture in loop reactor 101 within a defined range. Such cooling may include passage of a cooling media through reservoirs or coils thermally conductively coupled to the loop reactor 101 or a conduit which has diverted a portion of the multi-phase mixture out of the loop reactor 101 to a heat transfer unit operation 116. In at least some instances, control subsystem 290 may control the flow rate or temperature of the cooling media passed through the reservoirs or coils that are thermally conductively coupled to loop reactor 101 or a conduit which has diverted a portion of the multi-phase mixture out of loop reactor 101 to a heat transfer unit operation 116. In other instances, the heat produced by the microbiological species may be insufficient to maintain the multi-phase mixture in loop reactor 101 within a desired temperature range. Such may occur, for example, in extremely cold environments where loop reactor 101 is located in an exposed or partially exposed exterior location. In some instances, the reservoirs or coils thermally conductively coupled to loop reactor 101 or the conduit which has diverted portion of the multi-phase mixture out of loop reactor 101 to a heat transfer unit operation 116 may be used to warm the multi-phase mixture. In at least some instances, control subsystem 290 may control the flow rate or temperature of the warming media passed through the reservoirs or coils 140 that are thermally conductively coupled to the loop reactor 101 or the conduit which has diverted a portion of the multi-phase mixture out of the loop reactor 101 to a heat transfer unit operation 116.

At 510, the pressure on the gas substrate bubbles traveling with the multi-phase mixture through loop reactor 101 is decreased by flowing the multi-phase mixture through a first pressure reduction device. In some instances, the pressure on the gas substrate bubbles is decreased by flowing the multi-phase mixture through a first pressure reduction device that does not rely upon differences in hydrostatic pressure to cause a reduction in pressure. In other words, in some instances, the pressure on the gas substrate bubbles traveling with the multi-phase mixture through loop reactor 101 is decreased without a substantial change in the elevation of the centerline of the loop reactor 101 at the exit of the first pressure reduction zone 108 relative to the elevation of the centerline of the loop reactor 101 at the entrance to the first pressure reduction zone 108. The pressure decrease at 510 can, in some instances, advantageously increase the rate at which gas substrate bubbles and other gases desorb from the multi-phase mixture.

At 512, the multi-phase mixture exits first pressure reduction zone 108 and flows to the gas/liquid separation vessel 102. Gaseous material that has desorbed from the multi-phase mixture can also flow to the gas/liquid separation vessel 102 along with the multi-phase mixture. The multi-phase mixture entering the gas/liquid separation vessel 102 can include, but is not limited to the liquid containing unabsorbed nutrients, microorganisms and gas substrate bubbles containing undissolved and unabsorbed gas substrate. Gases and liquid entering gas/liquid separation vessel 102 separate into a gas phase and a liquid phase within gas/liquid separation vessel 102. Gases can be collected from the headspace of gas/liquid separation vessel 102 while liquid can be removed from the bottom of gas/liquid separation vessel 102. In addition to liquid, microorganisms can also be collected in gas/liquid separation vessel 102 and removed from the bottom thereof. The liquid and microorganisms removed from the bottom of gas/liquid separation vessel 102 can be delivered to the inlet 129 of fluid flow unit operation 104 for recirculation through loop reactor 101. In at least some instances, at least a portion of the collected gas may be subsequently processed or separated. At least a portion of the collected gas may be recycled to the loop reactor as a gas substrate. In some instances, at least a portion of the collected gas may be sold or otherwise disposed of. In at least some instances, at least a portion of the collected gas may be sold or traded as a fungible commodity. In at least some instances, the collected gas may include one or more $C_{2+}$ hydrocarbon gases and compounds based thereupon having value as either a finished product or as a raw material in a subsequent process. In some instances, the reactor is used to produce natural or non-natural products, such as ethanol, acetate, butanol, isoprene, propylene, farnesene, enzymes, or other metabolites or cellular products wherein the product is derived from a microorganism. In such cases, the products may be present in either the gas effluent 123 or the liquid effluent 125 depending on the physical properties of the product.

In at least some instances, at least a portion of the collected liquid may be subsequently processed or separated. For example, at least a portion of the liquid separated from the multi-phase mixture, which may or may not include biosolids, can be recycled through loop reactor 101. For example, at least a portion of the separated liquid containing biosolids may be combined with additional liquids and flowed through the loop reactor 101. Such recycle may advantageously provide an ongoing, continuous or semi-continuous, inoculation of the loop reactor 101 with established biological species. In some instances, at least a portion of the separated liquid may be collected and sold or otherwise disposed of. In at least some instances, at least a portion of the separated liquid may be sold or traded as a fungible commodity. In at least some instances, the separated liquid may include one or more $C_{2+}$ hydrocarbon liquids, including but not limited to one or more alcohols, glycols, or ketones.

At 514, microorganisms from gas/liquid separation vessel 102 can be removed upstream of fluid flow unit operation 104 or downstream of fluid flow unit operation 104, for example, at biomass removal port 128. The collected microorganisms can be further processed to recover desired products. In some instances, the microorganisms collected via biomass removal port 128 can be introduced to a separation subsystem 250 for processing and recovery of desired products.

Figure 6:
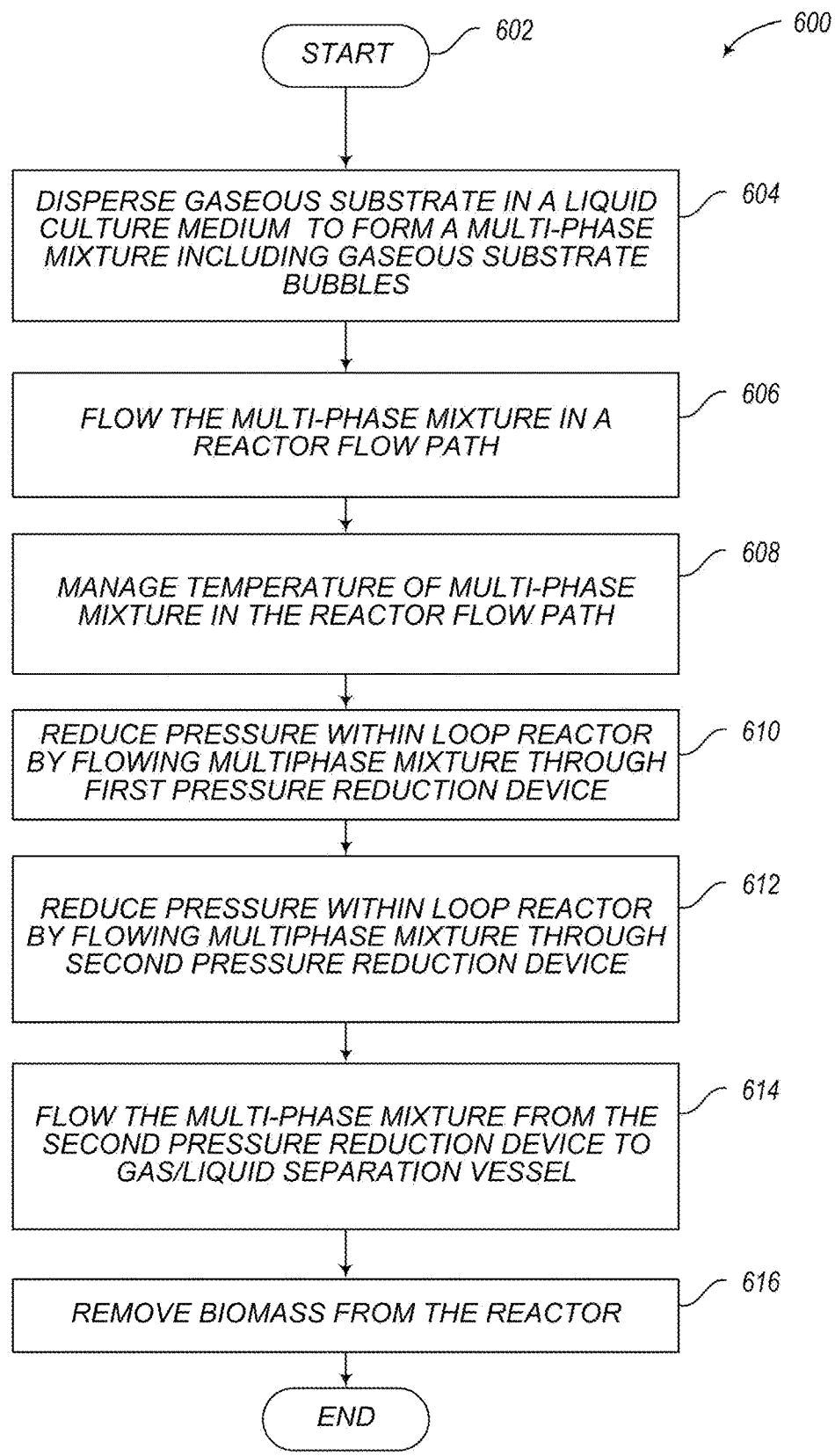
FIG. 6 shows a high level flow diagram of a fermentation process that includes flowing a multi-phase mixture through a first pressure reduction zone and a second pressure reduction zone of a loop reactor, according to one or more illustrated and/or described embodiments.

FIG. 6 shows a high level method for stimulating production of biomass 600 that utilizes a system 100 including one or more loop reactors 101 described in detail above with regard to FIGS. 2-4. The example biomass production method 600 uses identical or nearly identical steps to those described in detail with regard to the method for stimulating production of biomass method 500 discussed in detail with reference to FIG. 5, with the exception that the method for stimulating the production of biomass method 600 includes a step of reducing the pressure on the gas bubbles within the multi-phase mixture in the loop reactor by passing the multi-phase mixture through a second pressure reduction zone. The descriptions of steps 502, 504, 506, 508 and 510 in FIG. 5 apply to steps 602, 604, 606, 608 and 610 of FIG. 6, respectively. The description of step 514 of FIG. 5 applies to step 616 of FIG. 6.

At 612 in FIG. 6, the pressure on the gas substrate bubbles traveling with the multi-phase mixture through loop reactor 101 is decreased by flowing the multi-phase mixture from the first pressure reduction zone 108 to a second pressure reduction zone 112. In some instances, at 612, the pressure on the gas substrate bubbles is decreased by flowing the multi-phase mixture through a second pressure reduction device that does not rely upon differences in hydrostatic pressure to cause a reduction in pressure. In other words, in some instances, at 612, the pressure on the gas substrate bubbles traveling with the multi-phase mixture through loop reactor 101 is decreased without a substantial change in the elevation of the centerline of the loop reactor 101 at the exit of the second pressure reduction zone 112 relative to the elevation of the centerline of the loop reactor 101 at the entrance to the second pressure reduction zone 112. In other instances, at 612, the pressure on the gas substrate bubbles is decreased by flowing the multi-phase mixture through a second pressure reduction zone 108 that does rely upon differences in hydrostatic pressure to cause a reduction in pressure. In other words, in some instances, at 612, the pressure on the gas substrate bubbles traveling with the multi-phase mixture through loop reactor 101 is decreased by causing a change in the elevation of the centerline of the loop reactor 101 at the exit of the second pressure reduction zone 112 relative to the elevation of the centerline of the loop reactor 101 at the entrance to the second pressure reduction zone 112. In some instances, when pressure on the gas substrate bubbles is reduced at both steps 610 and 612, the magnitude of the pressure decrease at 612 can be less compared to the magnitude of the pressure decrease at 610. In some instances, these decreases in pressure advantageously increase the rate at which gas substrate bubbles and other gases desorb from the multi-phase mixture.

At 614, the multi-phase mixture from first pressure reduction zone 108 which has entered second pressure reduction zone 112 or 113 exits second pressure reduction zone 112 or 113 and flows to the gas/liquid separation vessel 102. Gaseous material that has desorbed from the multi-phase mixture can also flow to the gas/liquid separation vessel 102 along with the multi-phase mixture. The multi-phase mixture entering the gas/liquid separation vessel 102 can include, but is not limited to the liquid containing unabsorbed nutrients, microorganisms and gas substrate bubbles containing undissolved and unabsorbed gas substrate. Gases and liquid entering gas/liquid separation vessel 102 separate into a gas phase and a liquid phase within gas/liquid separation vessel 102. Gases can be collected from the headspace of gas/liquid separation vessel 102 while liquid can be removed from the bottom of gas/liquid separation vessel 102. In addition to liquid, microorganisms can also be collected in gas/liquid separation vessel 102 and removed from the bottom thereof. The liquid and microorganisms removed from the bottom of gas/liquid separation vessel 102 can be delivered to the inlet 129 of fluid flow unit operation 104 for recirculation through loop reactor 101. In at least some instances, at least a portion of the collected gas may be subsequently processed or separated. At least a portion of the collected gas may be recycled to the loop reactor as a gas substrate. In some instances, at least a portion of the collected gas may be sold or otherwise disposed of. In at least some instances, at least a portion of the collected gas may be sold or traded as a fungible commodity. In at least some instances, the collected gas may include one or more $C_{2+}$ hydrocarbon gases and compounds based thereupon having value as either a finished product or as a raw material in a subsequent process. In some instances, the reactor is used to produce natural or non-natural products, such as ethanol, acetate, butanol, isoprene, propylene, farnesene, enzymes, or other metabolites or cellular products wherein the product is derived from a microorganism. In such cases, the products may be present in either the gas effluent 123 or the liquid effluent 125 depending on the physical properties of the product.

In at least some instances, at least a portion of the collected liquid may be subsequently processed or separated. For example, at least a portion of the liquid separated from the multi-phase mixture, which may or may not include biosolids, can be recycled through loop reactor 101. For example, at least a portion of the separated liquid containing biosolids may be combined with additional liquids and flowed through the loop reactor 101. Such recycle may advantageously provide an ongoing, continuous or semi-continuous, inoculation of the loop reactor 101 with established biological species. In some instances, at least a portion of the separated liquid may be collected and sold or otherwise disposed of. In at least some instances, at least a portion of the separated liquid may be sold or traded as a fungible commodity. In at least some instances, the separated liquid may include one or more $C_{2+}$ hydrocarbon liquids, including but not limited to one or more alcohols, glycols, or ketones.

EXAMPLE

A microbial culture including *Methylococcus capsulatus* Bath co-cultured with a small amount of $C_2$ and $C_{3+}$ metabolizing microorganisms were processed in a system for stimulating the production of biomass that includes a loop reactor in accordance with embodiments described herein. The loop reactor included a non-vertical pressure reduction zone that included an adjustable flow control device in the form of a back pressure control valve. The flow rate and/or the pressure within the loop section of the reactor was controllable by opening or closing the valve. The loop reactor also included a desorption gas inlet between the gas/liquid separation vessel and the adjustable flow control device. The loop section of the loop reactor included five inlets for introducing oxygen gas and methane gas into the loop section. Two inlets for nitrogen gas and three inlets for ammonium hydroxide were present in the loop section downstream of the fluid flow unit operation and upstream of the adjustable flow control device. Inlets for acid, acid salt and alkali, such as sulphuric acid, phosphoric acid, sodium hydroxide, potassium hydroxide, ferrous sulphate, calcium chloride, magnesium, potassium and trace elements were present between the gas/liquid separation vessel and the pump. Two heat exchangers were utilized to provide heat transfer to and from the multi-phase mixture in the loop section as needed. The loop reactor was operated with the adjustable flow control device set for different flow rates through the adjustable flow control device. Steady state conditions, such as volumetric pump output, temperature of multi-phase mixture, pressure within loop section between the pump outlet and the adjustable flow control device, dissolved oxygen content of multi-phase mixture, oxygen volumetric flow rate into the loop section, volumetric flow rate of methane into the loop section, volumetric flow rate of nitrogen into the loop section, and/or pH of multi-phase mixture within the loop reactor varied depending upon the degree to which the control valve was open. With the flow rate through the control valve set at a specific level and the loop reactor in steady state operation, the following conditions were observed. Temperature within the loop reactor was measured to be about 45 degrees Celsius. pH of the multi-phase mixture at the inlet to the pump was about 6.2. pH of the multi-phase mixture at the inlet to the adjustable flow control device was about 5.3 and about 7.9 between the pump and the adjustable flow control device. Density of the multi-phase mixture was about 1.7 kg/m$^3$ at the outlet of the pump. Dissolved oxygen content varied from 0.07 to 0.36 ppm at different locations within the loop section. Pressure upstream of the pump was about 0.6-0.7 bar gauge. Pressure downstream of the pump was about 3.0 bar gauge. Pressure at the inlet to the adjustable flow control device was about 1.9 bar gauge and pressure within the headspace of the gas/liquid separation vessel was about 0.4 bar gauge.

The effect on biomass production rate in the loop reactor of increasing or decreasing the flow rate through the control valve and the pressure within the loop section of the reactor was evaluated. During steady state operation of the loop reactor, the opening of the control valve was varied so that the flow rate through the control valve and the pressure in the loop section of the loop reactor was increased or decreased. After the flow rate through the control valve was changed, the loop reactor was allowed to settle into steady state operation. After the loop reactor settled into steady state operation, data was collected to determine the loop reactor's production rate after the flow rate through the control valve and the pressure within the loop section was changed. The following is a summary of the findings of that evaluation.

Increasing the pressure within the loop section by reducing the flow rate through the control valve resulted in an increased biomass production rate in the loop reactor compared to the production rate before the flow rate through the control valve was decreased. Increasing the pressure within the loop section by reducing the flow rate through the control valve also produced higher pressures in the loop section between the control valve and the outlet of the pump and lower pressures in the loop section between the outlet of the control valve and the gas/liquid separation vessel. Decreasing the pressure within the loop section by increasing the flow rate through the control valve resulted in a decreased biomass production rate in the loop reactor compared to the production rate in the loop reactor before the flow rate through the control valve was increased. Decreasing the pressure within the loop section by increasing the flow rate through the control valve produced lower pressures in the loop section between the control valve and the outlet of the pump and higher pressures in the loop section between the outlet of the control valve and the gas/liquid separation vessel. This example illustrates how systems for stimulating the production of biomass that include a loop reactor in accordance with embodiments described herein are able to adjust the rate at which biomass is produced in a loop reactor.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems for stimulating the production of biomass, fermentors and fermentation systems. Such systems for stimulating the production of biomass, fermentors and fermentation systems may include loop reactors or fermentors for purposes other than chemical intermediate production, and may include loop reactors, fermentors and fermentation systems useful in food or beverage production. Similarly, the ancillary systems described herein, including the cooling gas/liquid separation unit operation, fluid flow unit operation, nutrient supply subsystem, heat transfer unit operation and the control subsystem may include a single system, for example a package heat exchanger or package control system, or may include a custom designed subsystem including any number of subcomponents that are physically, fluidly, and communicably coupled in a manner facilitating the controlled production and distribution of cooling or warming media (i.e., by the heat transfer unit operation), facilitating the separation of at least a portion of the multi-phase mixture into a gas, liquid, and semi-solid for recycle or for recovery and subsequent processing or sale (i.e., by the gas/liquid separation unit operation). The control subsystem can include an integrated or distributed control system that provides monitoring, alarming, control, and control output for all or a portion of the biomass production system or any of the ancillary subsystems. The control subsystem may also include any number of individual loop controllers and the like for control of one or more aspects of the biomass production system or any of the ancillary subsystems.

The foregoing detailed description has set forth various embodiments of the devices and/or processes via the use of process flow diagrams and example methods. Insofar as such block diagrams, schematics, and examples contain one or more functions and/or operations, it will be understood by those skilled in the art that each function and/or operation within such block diagrams, flowcharts, or examples can be implemented, individually and/or collectively, using wide range of off-the-shelf or customized components that are well known to those of skill in the chemical engineering arts. The microbiological species listed herein are intended to provide a sample of the potential microbiological species that can be supported in a system for promoting the production of biomass and loop reactors as described herein.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A process for stimulating production of biomass comprising:
    flowing through a loop section of a loop reactor, a multi-phase mixture of a gas and a liquid culture medium, the multi-phase mixture containing a biomass, the loop section including a portion sloped upward in the direction of flow of the multi-phase mixture in the loop section and an outlet;
    introducing nutrients into the multi-phase mixture;
    introducing a carbon-containing gas into the multi-phase mixture;
    passing the multi-phase mixture of a gas and a liquid culture medium from the loop section of the loop reactor into a first non-vertical pressure reduction zone of the loop reactor, the first non-vertical pressure reduction zone of the loop reactor including an eccentric expander that includes an inner diameter that transitions from a first end having a first diameter to a second end having a second diameter larger than the first diameter and an edge extending between the first end and a beginning of the second end that is parallel to a portion of the loop section to which the first non-vertical pressure reduction zone is connected;
    separating the multi-phase mixture of a gas and a liquid culture medium into a gas phase and a liquid phase in the first non-vertical pressure reduction zone;
    flowing the gas phase and the liquid phase separated from the multi-phase mixture of a gas and a liquid culture medium into a gas/liquid separation vessel; and
    removing the liquid phase from an outlet of the gas/liquid separation vessel and delivering the removed liquid phase to an inlet of the loop section.

2. The process of claim 1, wherein the passing the multi-phase mixture of a gas and a liquid culture medium into the first non-vertical pressure reduction zone of the loop reactor includes passing the multi-phase mixture of a gas and a liquid culture medium into a pipe section of the eccentric expander, the pipe section having a constant inner diameter.

3. The process of claim 2, wherein the passing the multi-phase mixture of a gas and a liquid culture medium into the first non-vertical pressure reduction zone of the loop reactor includes passing the multi-phase mixture of a gas and a liquid culture medium into an eccentric expander section of the eccentric expander.

4. The process of claim 3, wherein the first inner diameter is equal to the constant inner diameter of the pipe section.

5. The process of claim 4, further comprising passing the multi-phase mixture of a gas and a liquid culture medium through a control valve before passing the multi-phase mixture of a gas and a liquid culture medium into the pipe section.

6. The process of claim 1, further comprising introducing a desorption gas into a non-vertical portion of the loop section.

7. The process of claim 1, flowing the multi-phase mixture of a gas and a liquid culture medium from a control valve to the eccentric expander.

8. The process of claim 1, further comprising flowing the multi-phase mixture through a control valve before flowing the multi-phase mixture into the first pressure reduction zone including the eccentric expander.

9. The process of claim 1, further comprising flowing the multi-phase mixture of a gas and a liquid culture medium through an eccentric reducer prior to flowing the multi-phase mixture of a gas and a liquid culture medium into the eccentric expander.

10. A process for stimulating production of biomass comprising:
    flowing through a loop section of a loop reactor, a multi-phase mixture of a gas and a liquid culture medium, the multi-phase mixture containing a biomass, the loop section including an outlet;
    introducing nutrients into the multi-phase mixture;
    introducing a carbon-containing gas into the multi-phase mixture;
    passing the multi-phase mixture of a gas and a liquid culture medium from the loop section of the loop reactor into a first non-vertical pressure reduction zone of the loop reactor, the first non-vertical pressure reduction zone of the loop reactor including an eccentric expander that includes an inner diameter that transitions from a first end having a first diameter to a second end having a second diameter larger than the first diameter and an edge extending between the first end and a beginning of the second end that is parallel to a portion of the loop section to which the first non-vertical pressure reduction zone is connected;
    separating the multi-phase mixture of a gas and a liquid culture medium into a gas phase and a liquid phase in the first non-vertical pressure reduction zone;
    flowing the gas phase and the liquid phase separated from the multi-phase mixture of a gas and a liquid culture medium into a gas/liquid separation vessel; and
    removing the liquid phase from an outlet of the gas/liquid separation vessel and delivering the removed liquid phase to an inlet of the loop section.

11. The process of claim 10, wherein the eccentric expander includes a pipe section having a constant inner diameter.

12. The process of claim 10, wherein the loop section includes a portion sloped downward in the direction of flow of the multi-phase mixture in the loop section.

13. The process of claim 12, wherein the loop section includes a portion sloped upward in the direction of flow of the multi-phase mixture in the loop section.

14. The process of claim 12, wherein the eccentric expander includes an eccentric expander section and a pipe section.

15. The process of claim 12, wherein the eccentric expander has a first end having a first inner diameter and a second end having a second inner diameter, the second inner diameter being larger than the first inner diameter, and the first inner diameter equal to a constant inner diameter of a control valve.

16. The process of claim 10, further comprising flowing the multi-phase mixture of a gas and a liquid culture medium through an eccentric reducer prior to flowing the multi-phase mixture of a gas and a liquid culture medium into the eccentric expander.

17. The process of claim 10, further comprising flowing the multi-phase mixture of a gas and a liquid culture medium through a control valve before flowing the multi-phase mixture of a gas and a liquid culture medium into the eccentric expander.

18. The process of claim 17, further comprising flowing the multi-phase mixture of a gas and a liquid culture medium through an eccentric reducer before flowing the multi-phase mixture of a gas and a liquid culture medium into the control valve.

\* \* \* \* \*